United States Patent
Kalinski et al.

(10) Patent No.: US 10,815,457 B2
(45) Date of Patent: Oct. 27, 2020

(54) ACTIVE CXCR4+ IMMUNE CELLS AND METHODS FOR THEIR PRODUCTION AND USE

(71) Applicant: UNIVERSITY OF PITTSBURGH—OF THE COMMONWEALTH SYSTEM OF HIGHER EDUCATION, Pittsburgh, PA (US)

(72) Inventors: Pawel Kalinski, Wexford, PA (US); Ravikumar Muthuswamy, Monroeville, PA (US)

(73) Assignee: UNIVERSITY OF PITTSBURGH OF THE COMMONWEALTH SYSTEMS OF HIGHER EDUCATION, Pittsburgh, PA (US)

( * ) Notice: Subject to any disclaimer, the term of this patent is extended or adjusted under 35 U.S.C. 154(b) by 137 days.

(21) Appl. No.: 15/529,124

(22) PCT Filed: Nov. 24, 2015

(86) PCT No.: PCT/US2015/062357
§ 371 (c)(1),
(2) Date: May 24, 2017

(87) PCT Pub. No.: WO2016/085946
PCT Pub. Date: Jun. 2, 2016

(65) Prior Publication Data
US 2017/0260507 A1    Sep. 14, 2017

Related U.S. Application Data

(60) Provisional application No. 62/083,715, filed on Nov. 24, 2014.

(51) Int. Cl.
| | |
|---|---|
| *C12N 5/02* | (2006.01) |
| *C12N 5/0783* | (2010.01) |
| *A61K 35/17* | (2015.01) |
| *C12N 5/071* | (2010.01) |

(52) U.S. Cl.
CPC ............ *C12N 5/0638* (2013.01); *A61K 35/17* (2013.01); *C12N 5/0602* (2013.01); *C12N 5/0636* (2013.01); *C12N 5/0637* (2013.01); *C12N 2500/02* (2013.01); *C12N 2501/2312* (2013.01); *C12N 2501/60* (2013.01)

(58) Field of Classification Search
None
See application file for complete search history.

(56) References Cited

U.S. PATENT DOCUMENTS 10,316,289 B2 *   6/2019   Gattinoni ............... A61K 35/17

OTHER PUBLICATIONS

Walker et al ( Neuro-Oncology, 2014, v.16 pp. iii40.*
Clambey et. Al., ( J of Immunology, 2013,v.190, p. 208.8.*
Beyer, et al., 2009. Review Hypoxia. Hypoxia in the pathogenesis of systemic sclerosis. Arthritis Research and Therapy 11:220.
Brown, et al., 2005. COX-2: a molecular target for colorectal cancer prevention. Journal of clinical oncology: official journal of the American Society of Clinical Oncology 23:2840-2855.
Bruchard, et al., 2014. Tumor microenvironment: regulatory cells and immunosuppressive cytokines. Medicine Sciences 30:429-435. English Abstract.
Burger, et al., 2006. CXCR4: a key receptor in the crosstalk between tumor cells and their microenvironment. Blood 107:1761-1767.
Carbajo-Pescador, et al., 2013. Inhibition of VEGF expression through blockade of Hif1alpha and STAT3 signalling mediates the anti-angiogenic effect of melatonin in HepG2 liver cancer cells. British journal of cancer 109:83-91.
Ceradini, et al., 2005. Homing to hypoxia: HIF-1 as a mediator of progenitor cell recruitment to injured tissue. Trends Cardiovasc Med 15:57-63.
Conley-Lacomb, et al., 2013. PTEN loss mediated Akt activation promotes prostate tumor growth and metastasis via CXCL12/CXCR4 signaling. Molecular Cancer 12:85.
Couzin-Frankel, J. 2013. Breakthrough of the year 2013. Cancer Immunotherapy. Science 342:1432-1433.
Curiel, et al., 2004. Specific recruitment of regulatory T cells in ovarian carcinoma fosters immune privilege and predicts reduced survival. Nature Medicine 10:942-949.
Dai, et al., 2013. Preconditioning and post-treatment with cobalt chloride in rat model of perinatal hypoxic-ischemic encephalopathy. Brain & Development 36:3, 228-240.
Dejean, et al., 2012. ALK+ALCLs induce cutaneous, HMGB-1-dependent IL-8/CXCL8 production by keratinocytes through NF-kappaB activation. Blood 119:4698-4707.
Du, et al. 2008. HIF1alpha induces the recruitment of bone marrow-derived vascular modulatory cells to regulate tumor angiogenesis and invasion. Cancer Cell 13:206-220.
Dudley, 2011. Adoptive cell therapy for patients with melanoma. Journal of Cancer 2:360-362.
Faget, et al. 2011. Early detection of tumor cells by innate immune cells leads to T(reg) recruitment through CCL22 production by tumor cells. Cancer Research 71:6143-6152.
Fang, et al. 2009. Hypoxia inducible factors 1 and 2 are important transcriptional effectors in primary macrophages experiencing hypoxia. Blood 114:844-859.
Folkins, et al., 2009. Glioma tumor stem-like cells promote tumor angiogenesis and vasculogenesis via vascular endothelial growth factor and stromal-derived factor 1. Cancer Res 69:7243-7251.

(Continued)

*Primary Examiner* — Michail A Belyavskyi
(74) *Attorney, Agent, or Firm* — Meunier Carlin & Curfman LLC

(57) ABSTRACT

Provided herein are active $CXCR4^+$ $CD8^+$ T cells, active $CXCR4^+$ type-1 $CD4^+$ T cells and active $CXCR4^+$ NK cells and populations of those cells, methods for making active $CXCR4^+$ T cells and NK cells and populations of those cells, and methods for using active $CXCR4^+$ T cells and NK cells and populations of those cells for the treatment of cancer, precancerous conditions and chronic infections.

13 Claims, 8 Drawing Sheets
Specification includes a Sequence Listing.

(56) References Cited

OTHER PUBLICATIONS

Fridman, et al., 2011. Prognostic and predictive impact of intra- and peritumoral immune infiltrates. Cancer Research 71:5601-5605.

Fridman, et al., 2012. The immune contexture in human tumours: impact on clinical outcome. Nature Reviews. Cancer 12:298-306.

Fujiwara, H. 2014. Adoptive T-cell therapy for hematological malignancies using T cells gene-modified to express tumor antigen-specific receptors. International Journal of Hematology 99:123-131.

Galli, et al., 1998. Enhanced HIV expression during Th2-oriented responses explained by the opposite regulatory effect of IL-4 and IFN-gamma of fusin/CXCR4. European Journal of Immunology 28:3280-3290.

Galon, et al., 2006. Type, density, and location of immune cells within human colorectal tumors predict clinical outcome. Science 313:1960-1964.

Galon, et al., 2007. The adaptive immunologic microenvironment in colorectal cancer: a novel perspective. Cancer Research 67:1883-1886.

Ganesan, et al., 2013. Tumor-infiltrating regulatory T cells inhibit endogenous cytotoxic T cell responses to lung adenocarcinoma. J Immunol 191:2009-2017.

Greenhough, et al., 2009. The COX-2/PGE2 pathway: key roles in the hallmarks of cancer and adaptation to the tumour microenvironment. Carcinogenesis 30:377-386.

Grover, et al., 2006. Intralymphatic dendritic cell vaccination induces tumor antigen-specific, skin-homing T lymphocytes. Clinical cancer research: An official journal of the American Association for Cancer Research 12:5801-5808.

Harlin, et al., 2009. Chemokine expression in melanoma metastases associated with CD8+ T-cell recruitment. Cancer Research 69:3077-3085.

Harris, et al., 2002. Hypoxia—a key regulatory factor in tumor growth. Nature Reviews. Cancer 2:38-47.

Harris, et al., 2008. The interferon-gamma-mediated inhibition of lipoprotein lipase gene transcription in macrophages involves casein kinase 2- and phosphoinositide-3-kinase-mediated regulation of transcription factors Sp1 and Sp3. Cellular Signaling 20:2296-2301.

Jun., et al., 2012. T-cell therapy at the threshold. Nat. Biotechnol. 30:611-614.

Jun., C.H. 2007. Adoptive T cell therapy for cancer in the clinic. The Journal of Clinical Investigation 117:1466-1476.

Kalos, et al., 2011. T cells with chimeric antigen receptors have potent antitumor effects and can establish memory in patients with advanced leukemia. Sci Transl Med 3:95ra73.

Kershaw, et al., 2002. Redirecting migration of T cells to chemokine secreted from tumors by genetic modification with CXCR2. Human Gene Therapy 13:1971-1980.

Khong, et al., 2013. Identification of the angiogenic gene signature induced by EGF and hypoxia in colorectal cancer. BMC Cancer 13:518.

Kim, et al. 2006. Chemokine receptor CXCR4 expression in patients with melanoma and colorectal cancer liver metastases and the association with disease outcome. Annals of Surgery 244:113-120.

Kim, et al., 2005. Chemokine receptor CXCR4 expression in colorectal cancer patients increases the risk for recurrence and for poor survival. Journal of Clinical Oncology: official journal of the American Society of Clinical Oncology 23:2744-2753.

Kohler, et al., 2012. Influence of hypoxia-inducible factor 1alpha on dendritic cell differentiation and migration. European Journal of Immunology 42:1226-1236.

Kunz, et al., 1999. Strong expression of the lymphoattractant C-X-C chemokine Mig is associated with heavy infiltration of T cells in human malignant melanoma. The Journal of Pathology 189:552-558.

Leslie, et al., 2007. Immunization against MUC18/MCAM, a novel antigen that drives melanoma invasion and metastasis. Gene Therapy 14:316-323.

Liddy, et al. 2012. Monoclonal TCR-redirected tumor cell killing. Nat Med 18:980-987.

Lou, et al., 2004. Dendritic cells strongly boost the antitumor activity of adoptively transferred T cells in vivo. Cancer Research 64:6783-6790.

Luan, et al., 1997. Mechanism and biological significance of constitutive expression of MGSA/GRO chemokines in malignant melanoma tumor progression. Journal of Leukocyte Biology 62:588-597.

Mackensen, et al., 2006. Phase I study of adoptive T-cell therapy using antigen-specific CD8+ T cells for the treatment of patients with metastatic melanoma. Journal of clinical oncology: official journal of the American Society of Clinical Oncology 24:5060-5069.

Maes, et al., 2013. Depletion of regulatory T cells in a mouse experimental glioma model through anti-CD25 treatment results in the infiltration of non-immunosuppressive myeloid cells in the brain. Clinical & Developmental Immunology 2013:952469.

McLean, et al. 2011. The inflammatory microenvironment in colorectal neoplasia. PloS One 6:e15366.

McNutt, 2013. Cancer immunotherapy. Science 342:1417.

Mead, et al., 2003. Interferon-gamma stimulates the expression of the inducible cAMP early repressor in macrophages through the activation of casein kinase 2. A potentially novel pathway for interferon-gamma-mediated inhibition of gene transcription. The Journal of Biological Chemistry 278:17741-17751.

Melenhorst, et al., 2006. Robust expansion of viral antigen-specific CD4+ and CD8+ T cells for adoptive T cell therapy using gene-modified activated T cells as antigen presenting cells. Journal of Immunotherapy 29:436-443.

Mizokami, et al., 2004. Stromal cell-derived factor-1alpha-induced cell proliferation and its possible regulation by CD26/dipeptidyl peptidase IV in endometrial adenocarcinoma. International journal of cancer. Journal International Du Cancer 110:652-659.

Mlecnik, et al. 2010. Biomolecular network reconstruction identifies T-cell homing factors associated with survival in colorectal cancer. Gastroenterology 138:1429-1440.

Murdoch, et al., 2004. Mechanisms regulating the recruitment of macrophages into hypoxic areas of tumors and other ischemic tissues. Blood 104:2224-2234.

Muthuswamy, et al., 2012. NF-kappaB hyperactivation in tumor tissues allows tumor-selective reprogramming of the chemokine microenvironment to enhance the recruitment of cytolytic T effector cells. Cancer Research 72:3735-3743.

Obermajer, et al., 2011. PGE(2)-induced CXCL12 production and CXCR4 expression controls the accumulation of human MDSCs in ovarian cancer environment. Cancer Research 71:7463-7470.

Ogle, et al., 2012. Inhibition of prolyl hydroxylases by dimethyloxaloylglycine after stroke reduces ischemic brain injury and requires hypoxia inducible factor-1alpha. Neurobiology of Disease 45:733-742.

Ohtani, et al., 2009. Abundant expression of CXCL9 (MIG) by stromal cells that include dendritic cells and accumulation of CXCR3+ T cells in lymphocyte-rich gastric carcinoma. The Journal of Pathology 217:21-31.

Pages, et al. 2005. Effector memory T cells, early metastasis, and survival in colorectal cancer. The New England Journal of Medicine 353:2654-2666.

Pages, et al. 2009. In situ cytotoxic and memory T cells predict outcome in patients with early-stage colorectal cancer. Journal of clinical oncology: official journal of the American Society of Clinical Oncology 27:5944-5951.

Pan, et al., 2008. Reversion of immune tolerance in advanced malignancy: modulation of myeloid-derived suppressor cell development by blockade of stem-cell factor function. Blood 111:219-228.

Park, et al., 2011. Induction of TLR4-dependent CD8+ T cell immunity by murine beta-defensin2 fusion protein vaccines. Vaccine 29:3476-3482.

Peng, et al. 2010. Transduction of tumor-specific T cells with CXCR2 chemokine receptor improves migration to tumor and antitumor immune responses. Clinical cancer research: an official journal of the American Association for Cancer Research 16:5458-5468.

(56) References Cited

OTHER PUBLICATIONS

Ping, et al. 2011. The chemokine CXCL12 and its receptor CXCR4 promote glioma stem cell-mediated VEGF production and tumour angiogenesis via PI3K/AKT signalling. J Pathol 224:344-354.
Radvanyi, et al., 2012. Specific lymphocyte subsets predict response to adoptive cell therapy using expanded autologous tumor-infiltrating lymphocytes in metastatic melanoma patients. Clinical cancer research : an official journal of the American Association for Cancer Research 18:6758-6770.
Richard, et al., 2007. 15-Deoxy-delta(12,14)-prostaglandin J(2) down-regulates CXCR4 on carcinoma cells through PPARgamma- and NFkappaB-mediated pathways. Experimental Cell Research 313:3446-3458.
Rosenberg, et al. 1999. Impact of cytokine administration on the generation of antitumor reactivity in patients with metastatic melanoma receiving a peptide vaccine. Journal of Immunology 163:1690-1695.
Rosenberg, et al. 1998. Immunizing patients with metastatic melanoma using recombinant adenoviruses encoding MART-1 or gp100 melanoma antigens. Journal of the National Cancer Institute 90:1894-1900.
Salcedo, et al., 2003. Angiogenic effects of prostaglandin E2 are mediated by up-regulation of CXCR4 on human microvascular endothelial cells. Blood 102:1966-1977.
Sallusto, et al., 2004. Chemoattractants and their receptors in homeostasis and inflammation. Curr Opin Immunol 16:724-731.
Sallusto, et al., 1998. Flexible programs of chemokine receptor expression on human polarized T helper 1 and 2 lymphocytes. J Exp Med 187:875-883.
Sallusto, et al., 1997. Selective expression of the eotaxin receptor CCR3 by human T helper 2 cells. Science 277:2005-2007.
Sallusto, et al., 2000. The role of chemokine receptors in primary, effector, and memory immune responses. Annu Rev Immunol 18:593-620.
Schaible, et al., 2013. Hypoxia modulates infection of epithelial cells by Pseudomonas aeruginosa. PloS One 8:e56491.
Schioppa, et al. 2003. Regulation of the chemokine receptor CXCR4 by hypoxia. The Journal of Experimental Medicine 198:1391-1402.
Scotton, et al., 2002. Multiple actions of the chemokine CXCL12 on epithelial tumor cells in human ovarian cancer. Cancer Research 62:5930-5938.
Semenza, 2003. Targeting HIF-1 for cancer therapy. Nature reviews. Cancer 3:721-732.
Sica, et al., 2011. Hypoxia: a double-edged sword of immunity. J Mol Med (Berl) 89:657-665.
Sinha, et al., 2007. Cross-talk between myeloid-derived suppressor cells and macrophages subverts tumor immunity toward a type 2 response. Journal of Immunology 179:977-983.
Staller, et al., 2003. Chemokine receptor CXCR4 downregulated by von Hippel-Lindau tumour suppressor pVHL. Nature 425:307-311.
Verbeke, et al. 2010. Expression of angiostatic platelet factor-4var/CXCL4L1 counterbalances angiogenic impulses of vascular endothelial growth factor, interleukin-8/CXCL8, and stromal cell-derived factor 1/CXCL12 in esophageal and colorectal cancer. Human Pathology 41:990-1001.
Voron, et al., 2014. Control of the Immune Response by Pro-Angiogenic Factors. Frontiers in Oncology 4:70.
Wang, et al., 2006. CXCL1 induced by prostaglandin E2 promotes angiogenesis in colorectal cancer. The Journal of Experimental Medicine 203:941-951.
Wang, et al., 1998. IL-4 and a glucocorticoid up-regulate CXCR4 expression on human CD4+ T lymphocytes and enhance HIV-1 replication. Journal of Leukocyte Biology 64:642-649.
Weber, et al., 2011. White paper on adoptive cell therapy for cancer with tumor-infiltrating lymphocytes: a report of the CTEP subcommittee on adoptive cell therapy. Clinical cancer research: an official journal of the American Association for Cancer Research 17:1664-1673.
Weiss, et al., 2014. Regulatory T Cells and Myeloid-Derived Suppressor Cells in the Tumor Microenvironment Undergo Fas-Dependent Cell Death during IL-2/alphaCD40 Therapy. Journal of Immunology 192:5821-5829.
Yang, et al. 2012. TGF-beta-miR-34a-CCL22 signaling-induced Treg cell recruitment promotes venous metastases of HBV-positive hepatocellular carcinoma. Cancer Cell 22:291-303.
Zagzag, et al., 2006. Hypoxia-inducible factor 1 and VEGF upregulate CXCR4 in glioblastoma: implications for angiogenesis and glioma cell invasion. Laboratory Investigation 86:1221-1232.
Zou, et al. 2001. Stromal-derived factor-1 in human tumors recruits and alters the function of plasmacytoid precursor dendritic cells. Nature Medicine 7:1339-1346.
Cerdeira, AS et al. "Conversion of peripheral blood NK cells to a decidual NK-like phenotype by a cocktail of defined factors", J. Immunol, 2013, 190: 3939-3948.
Duchesneau, P. et al. Up-regulation of leukocyte CXCR4 expression by sulfatide: An L-selectin-dependent pathway on CD4+ T cells, Eur J Immunol, 2007, 37: 2949-2960.
Ikejiri, A. et al. "Dynamic regulation of Th17 differentiation by oxygen concentrations", International Immunology, 2011, 24: 137-146.
McNamee, En et al. "Hypoxia and hypoxia-inducible factors as regulators of T cell development, differentiation, and function", Immunol Res, 2013, 55: 58-70.
Yan, M. et al. "Recruitment of regulatory T cells in correlated with hypoxia-induced CXCR4 expression, and is associated with poor prognosis in basal-like breast cancers", Breast Cancer Research, 2011, 13: R47.
International Search Report dated Mar. 7, 2016, from International Application No. PCT/US2015/062357, 3 pages.
Mosser DM, Zhang X.; "Interleukin-10; new perspectives on an old cytokine."; Immunol Rev., Dec. 2008;226:205-18.
N. Kobayashi et al., "Down-regulation of CXCR4 expression on human CD8+ T cells during peripheral differentiation," Eur. J. Immunol. 2004 34: 3370-3378.

\* cited by examiner

SEQUENCE LISTING

<160> NUMBER OF SEQ ID NOS: 2

<210> SEQ ID NO 1
<211> LENGTH: 352
<212> TYPE: PRT
<213> ORGANISM: Homo sapiens

<400> SEQUENCE: 1

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Phe His Ser Ser
            340                 345                 350

<210> SEQ ID NO 2
<211> LENGTH: 247

-continued

```
<212> TYPE: PRT
<213> ORGANISM: Homo sapiens

<400> SEQUENCE: 2

Met Gln Pro Ile Leu Leu Leu Ala Phe Leu Leu Leu Pro Arg Ala
1               5                   10                  15

Asp Ala Gly Glu Ile Ile Gly Gly His Glu Ala Lys Pro His Ser Arg
            20                  25                  30

Pro Tyr Met Ala Tyr Leu Met Ile Trp Asp Gln Lys Ser Leu Lys Arg
        35                  40                  45

Cys Gly Gly Phe Leu Ile Arg Asp Asp Phe Val Leu Thr Ala Ala His
    50                  55                  60

Cys Trp Gly Ser Ser Ile Asn Val Thr Leu Gly Ala His Asn Ile Lys
65                  70                  75                  80

Glu Gln Glu Pro Thr Gln Gln Phe Ile Pro Val Lys Arg Pro Ile Pro
                85                  90                  95

His Pro Ala Tyr Asn Pro Lys Asn Phe Ser Asn Asp Ile Met Leu Leu
            100                 105                 110

Gln Leu Glu Arg Lys Ala Lys Arg Thr Arg Ala Val Gln Pro Leu Arg
        115                 120                 125

Leu Pro Ser Asn Lys Ala Gln Val Lys Pro Gly Gln Thr Cys Ser Val
    130                 135                 140

Ala Gly Trp Gly Gln Thr Ala Pro Leu Gly Lys His Ser His Thr Leu
145                 150                 155                 160

Gln Glu Val Lys Met Thr Val Gln Glu Asp Arg Lys Cys Glu Ser Asp
                165                 170                 175

Leu Arg His Tyr Tyr Asp Ser Thr Ile Glu Leu Cys Val Gly Asp Pro
            180                 185                 190

Glu Ile Lys Lys Thr Ser Phe Lys Gly Asp Ser Gly Gly Pro Leu Val
        195                 200                 205

Cys Asn Lys Val Ala Gln Gly Ile Val Ser Tyr Gly Arg Asn Asn Gly
    210                 215                 220

Met Pro Pro Arg Ala Cys Thr Lys Val Ser Ser Phe Val His Trp Ile
225                 230                 235                 240

Lys Lys Thr Met Lys Arg Tyr
                245
```

ACTIVE CXCR4+ IMMUNE CELLS AND METHODS FOR THEIR PRODUCTION AND USE

STATEMENT REGARDING FEDERALLY SPONSORED RESEARCH OR DEVELOPMENT

This invention was made with government support under CA132714 and CA121973 awarded by the National Institutes of Health. The government has certain rights in this invention.

BACKGROUND OF THE INVENTION

1) Field of the Invention

The fields of the invention are immunology, immunotherapy and treatment of cancer, premalignant lesions and chronic infections.

2) Description of Related Art

Cancer (or neoplastic disease) is the name we give to a mass of cells that grows in an abnormal, unregulated way and that ultimately overwhelms a body system or organ. A "tumor" refers to any abnormal growth of cells and can be harmless or dangerous. A harmless tumor is called benign and does not contain cancerous cells whereas a dangerous tumor is called malignant because it contains cancerous cells.

Cancers are further divided into carcinomas, sarcomas, leukemias or lymphomas, according to the cell types that are involved. For example, cancers that develop in skin cells or cells lining or covering the internal organs are called carcinomas whereas sarcomas develop in bone, cartilage, fat, muscle, blood vessels or connective tissue. Cancers of the lymphatic system that develop in mature immune system cells are called lymphomas or leukemias.

The development of tumors might be seen as a failure of immune surveillance. However, not all tumors are naturally immunogenic, and even among those that are immunogenic, the uncontrolled rapid growth of a cancer may sometimes out-run a robust immune response. Further, recent evidence suggests that tumors themselves have the ability to thwart the development of effective immune responses against cancer antigens.

Tumors manage to thwart the development of an effective immune response by attracting undesirable types of immune cells, such as myeloid-derived suppressor cells (MDSCs) and T regulatory cells (Tregs), known to protect tumors and promote their growth. Tumor-associated elevated production of $PGE_2$ [Greenhough, A., et al. 2009. The COX-2/$PGE_2$ pathway: key roles in the hallmarks of cancer and adaptation to the tumour microenvironment. Carcinogenesis 30:377-386; Brown, J. R., and DuBois, R. N. 2005. COX-2: a molecular target for colorectal cancer prevention. Journal of Clinical Oncology 23:2840-2855] and hypoxia [Harris, A. L. 2002. Hypoxia—a key regulatory factor in tumour growth. Nature reviews. Cancer 2:38-47; Semenza, G. L. 2003. Targeting HIF-1 for cancer therapy. Nature Reviews. Cancer 3:721-732], favors local secretion of CCL2 [Murdoch, C., et al. 2004. Mechanisms regulating the recruitment of macrophages into hypoxic areas of tumors and other ischemic tissues. Blood 104:2224-2234], CCL22 [Kohler, T., et al. 2012. Influence of hypoxia-inducible factor 1 alpha on dendritic cell differentiation and migration. European Journal of Immunology 42:1226-1236], CXCL8 and CXCL12, the chemokines preferentially attracting MDSCs and Tregs Tumors also suppress production of chemokines that attract classical type-1 effector cells ($CD8^+$ T cells, TH1 $CD4^+$ T cells and NK cells), which cells assist in or effect tumor control. [See Curiel, T. J., et al. 2004. Specific recruitment of regulatory T cells in ovarian carcinoma fosters immune privilege and predicts reduced survival. Nature Medicine 10:942-949; Faget, J., et al. 2011. Early detection of tumor cells by innate immune cells leads to T(reg) recruitment through CCL22 production by tumor cells. Cancer Research 71:6143-6152; Yang, P., et al. 2012. TGF-beta-miR-34a-CCL22 signaling-induced Treg cell recruitment promotes venous metastases of HBV-positive hepatocellular carcinoma. Cancer Cell 22:291-303; Zou, W., et al. 2001. Stromal-derived factor-1 in human tumors recruits and alters the function of plasmacytoid precursor dendritic cells. Nature Medicine 7:1339-1346; Murdoch, C., et al. 2004. Mechanisms regulating the recruitment of macrophages into hypoxic areas of tumors and other ischemic tissues. Blood 104:2224-2234.]

Suboptimal homing of type-1 effector $CD8^+$ T cells (typically referred to as cytotoxic T cells; CTLs) to tumors constitutes a significant obstacle to clinical effectiveness of the spontaneously-occurring and therapeutically-induced immunity against cancer. The ability of CTLs to enter transformed or infected tissues is critical for their ability to control cancer and a prerequisite for success of immunotherapies. Multiple recent studies have demonstrated the prognostic value of tumor infiltration with $CD8^+$ T cells in different groups of cancer patients [See Salcedo, R., et al. 2003. Angiogenic effects of prostaglandin E2 are mediated by up-regulation of CXCR4 on human microvascular endothelial cells. Blood 102:1966-1977; Pages, F., et al. 2005. Effector memory T cells, early metastasis, and survival in colorectal cancer. The New England journal of medicine 353:2654-2666; Galon, J., et al. 2006. Type, density, and location of immune cells within human colorectal tumors predict clinical outcome. Science 313:1960-1964; Galon, J., et al. 2007. The adaptive immunologic microenvironment in colorectal cancer: a novel perspective. Cancer Research 67:1883-1886; Pages, F., et al. 2009. In situ cytotoxic and memory T cells predict outcome in patients with early-stage colorectal cancer. Journal of Clinical Oncology 27:5944-5951; Mlecnik, B., et al. 2010. Biomolecular network reconstruction identifies T-cell homing factors associated with survival in colorectal cancer. Gastroenterology 138:1429-1440; Fridman, W. H., et al. 2011. Prognostic and predictive impact of intra- and peritumoral immune infiltrates. Cancer Research 71:5601-5605; Fridman, W. H., et al. 2012. The immune contexture in human tumours: impact on clinical outcome. Nature reviews. Cancer 12:298-306], suggesting that the ability of CTLs induced or applied as immunotherapies to migrate toward a tumor and to enter tumor tissues may be essential for their clinical effectiveness. [See Dudley, M. E. 2011. Adoptive cell therapy for patients with melanoma. Journal of Cancer 2:360-362; June, C. H. 2007. Adoptive T cell therapy for cancer in the clinic. The Journal of Clinical Investigation 117:1466-1476; Fujiwara, H. 2014. Adoptive T-cell therapy for hematological malignancies using T cells gene-modified to express tumor antigen-specific receptors. International Journal of Hematology 99:123-131; Lou, Y., et al. 2004. Dendritic cells strongly boost the antitumor activity of adoptively transferred T cells in vivo. Cancer Research 64:6783-6790; Leslie, M. C., et al. 2007. Immunization against MUC18/MCAM, a novel antigen that drives melanoma invasion and metastasis. Gene therapy 14:316-323; Rosenberg, S. A., et al. 1998. Immunizing patients with metastatic melanoma using recombinant adenoviruses encoding MART-1 or gp100 melanoma antigens. Journal of the National Cancer Institute 90:1894-1900; Rosenberg, S. A., et al. 1999. Impact of cytokine administration on the generation of antitumor reactivity in patients with metastatic melanoma receiving a peptide vaccine. Journal of Immunology 163:1690-1695; Park, H. J., et al. 2011. Induction of TLR4-dependent CD8+ T cell immunity by murine beta-defensin2 fusion protein vaccines. Vaccine 29:3476-3482; Grover, A., et al. 2006. Intralymphatic dendritic cell vaccination induces tumor antigen-specific, skin-homing T lymphocytes. Clinical Cancer Research 12:5801-5808; Mackensen, A., et al. 2006. Phase I study of adoptive T-cell therapy using antigen-specific CD8+ T cells for the treatment of patients with metastatic melanoma. Journal of Clinical Oncology 24:5060-5069. 19. Kershaw, M. H., Wang, G., et al. 2002. Redirecting migration of T cells to chemokine secreted from tumors by genetic modification with CXCR2. Human Gene Therapy 13:1971-1980; Melenhorst, J. J., et al. 2006. Robust expansion of viral antigen-specific CD4+ and CD8+ T cells for adoptive T cell therapy using gene-modified activated T cells as antigen presenting cells. Journal of Immunotherapy 29:436-443; discussion 365-436; Radvanyi, L. G., et al. 2012. Specific lymphocyte subsets predict response to adoptive cell therapy using expanded autologous tumor-infiltrating lymphocytes in metastatic melanoma patients. Clinical Cancer Research 18:6758-6770; Peng, W., et al. 2010. Transduction of tumor-specific T cells with CXCR2 chemokine receptor improves migration to tumor and antitumor immune responses. Clinical Cancer Research 16:5458-5468; Weber, J., et al. 2011. White paper on adoptive cell therapy for cancer with tumor-infiltrating lymphocytes: a report of the CTEP subcommittee on adoptive cell therapy. Clinical Cancer Research 17:1664-1673.]

To assure efficient tumor entry of CTLs, one either needs to reprogram tumor microenvironments to locally induce expression of CTL attracting chemokines or to induce CTLs to express chemokine receptors relevant to typical tumor microenvironments. However, modification of the CKR repertoire of CTLs to match chemokines expressed in tumor microenvironment (TEM) represents multiple obstacles. Since CTLs and Th1 cells do not naturally express CXCR1 or CXCR2, the receptors for CXCL8 and CXCL1/2, several groups have attempted to genetically manipulate patients' T cells to enforce their expression [Kershaw, M. H., Wang, G., et al. 2002. Redirecting migration of T cells to chemokine secreted from tumors by genetic modification with CXCR2. Human Gene Therapy 13:1971-1980; Peng, W., et al. 2010. Transduction of tumor-specific T cells with CXCR2 chemokine receptor improves migration to tumor and antitumor immune responses. Clinical Cancer Research 16:5458-5468]. Yet, genetic manipulation of cells for administration to a patient is difficult, time consuming, and expensive.

Further, the current paradigm of chemokine receptor regulation implies that the pattern of development of T cell effector functions (cytotoxic/type-1 versus non-cytotoxic/regulatory) determines the pattern of chemokine receptor expression and migratory pattern of the resulting T cells. Specifically, T cells differentiating in type-1 conditions (CTLs and Th1 cells, another type of antitumor T cells) have been shown to down regulate CXCR4, CCR4 and CCR2, the chemokine receptors capable of directing their migration to non-inflamed tumors. Similarly, activated natural killer (NK) cells are known to have type-1 homing pattern. This indicates that ex vivo or in vivo induction of T cells (or NK cells) with both the desirable cytotoxic/pro-inflammatory properties and the ability to enter typical tumor tissues will be difficult to achieve.

The paradigms and mechanisms of tumor-associated immune dysfunction are also relevant to chronic infections, including tuberculosis and AIDS (and infections with HPV, HBV, HCV, which often lead to premalignant states and tumor development), which, in contrast to acute infections, are associated with a shift from local predominance of pro-inflammatory cytokines to chemokines, to local predominance of anti-inflammatory factors in infected tissues.

Figure 5:
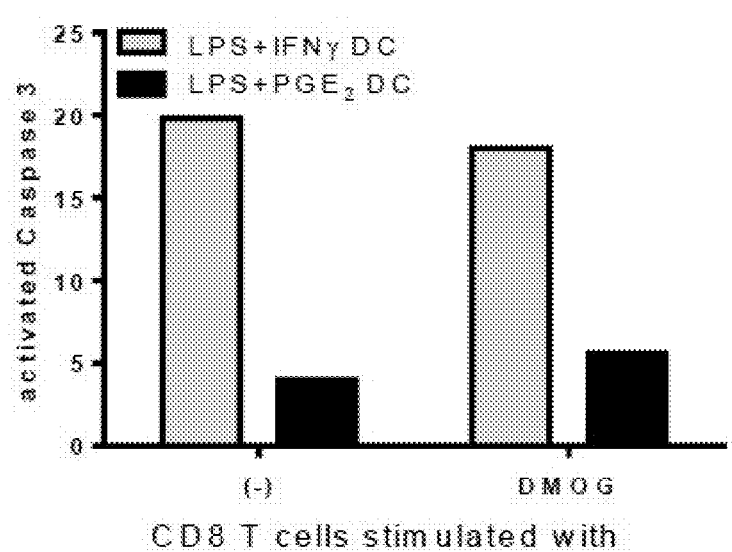

FIG. 5 shows that DMOG treatment does not impair cytolytic ability of cytotoxic CD8$^+$ T cells. Cytotoxic CD8$^+$ T cells generated in the indicated conditions were incubated with SEB-loaded target cells JY-1 cells at a 1:10 ratio for 4 hours at 37° C. After incubation, the cells were harvested and stained for activated Caspase-3 and CD33 (JY-1 cell marker). The histogram represents MFI of activated caspase-3 in JY1 cells (CD33-gated) incubated with CD8$^+$ T cells generated by stimulation with SEB pulsed LPS+IFNγ-matured DCs or LPS+PGE$_2$-matured DCs and further non-exposed or exposed to 200 µM DMOG treatment.

Figure 6A:
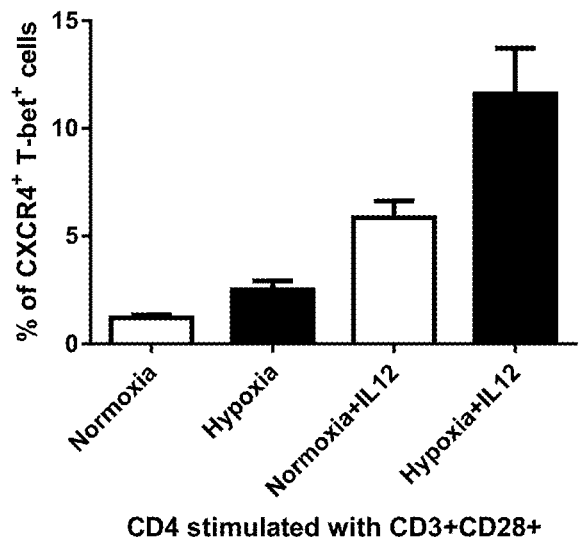
Figure 6B:
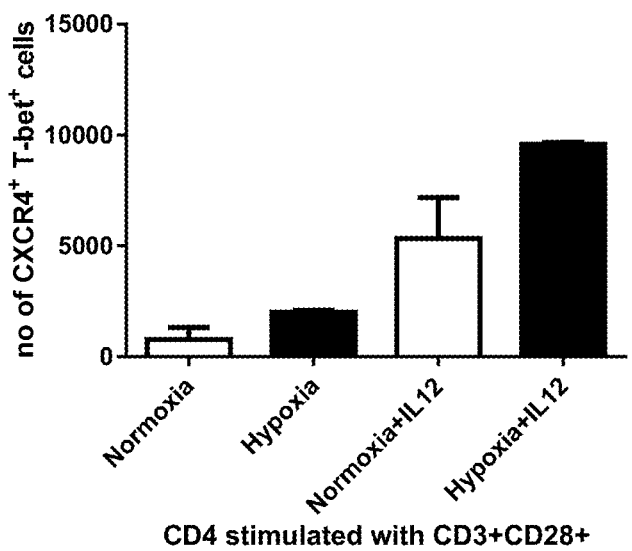

FIG. 6 (A, B) shows that hypoxia increases both the percentage and absolute numbers of T-bet, CXCR4 double positive CD4 effector Cells. CD4$^+$ T cells were isolated by negative selection, stimulated with CD3/CD28 beads without or with IL-12 for 5 days, then exposed to normoxia or hypoxia for additional 3 days, and on day 8 cells were harvested and stained for T-bet (Intra-cellular) and CXCR4. Percentage (A) and absolute numbers (B) of T-bet and CXCR4 double positive CD4$^+$ T cells were calculated by flow cytometry and are depicted in the figure.

Figure 7A:
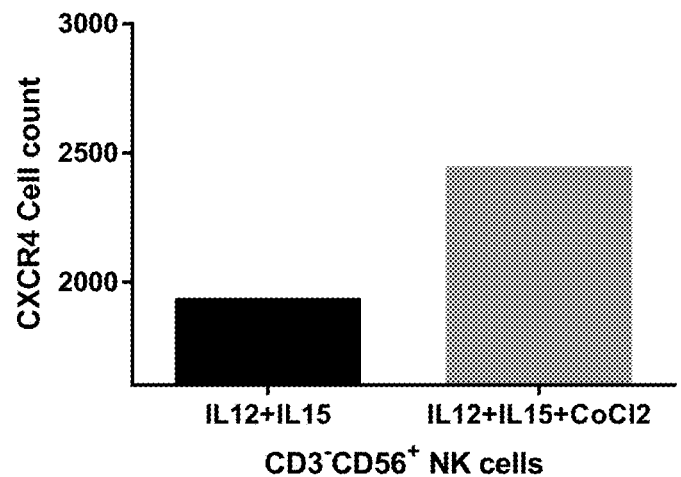
Figure 7B:
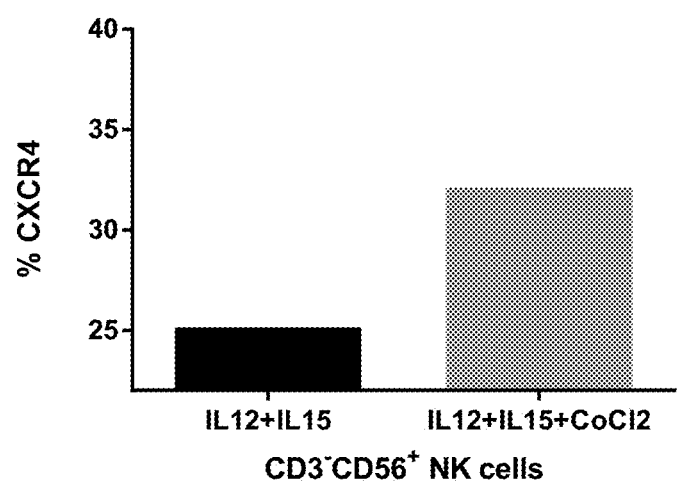

FIG. 7 (A, B) shows that CoCl2 increases CXCR4 expression on IL12+IL15-activated NK cells. Negatively Isolated (EasySep) NK cells were cultured overnight with NK cell activators, IL-12p70 (20 ng/ml) and IL-15 (20 ng/ml), in absence or presence of 200 µM CoCl$_2$ (Hypoxia mimic; HIF1α activator). Absolute numbers (A) and percentage (B) of CXCR4 NK cells are calculated by flow cytometry and are depicted in the figure.

DETAILED DESCRIPTION OF THE INVENTION

Provided herein are active CXCR4$^+$ CD8$^+$ T cells (including CTLs), active CXCR4$^+$ type-1 CD4$^+$ T cells (Th1 cells) and active (type-1: cytotoxic and/or IFNγ-producing) CXCR4$^+$ NK cells and populations of those cells, methods for making active CXCR4$^+$ T cells (including CTLs and Th1) and NK cells and populations of those cells, and methods for using active CXCR4$^+$ T cells and NK cells and populations of those cells for the treatment of cancer, precancerous conditions and chronic infections. Terms used throughout this application are to be construed with ordinary and typical meaning to those of ordinary skill in the art. However, Applicants desire that the following terms be given the particular definition as defined below.
Definitions As used in the specification and claims, the singular form "a," "an," and "the" include plural references unless the context clearly dictates otherwise. For example, the term "a cell" includes a plurality of cells, including mixtures thereof.

The term "administering" refers to an administration that is oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

As used herein, the term "active" when referring to a CD8$^+$ T cell or an NK cell includes or refers to a state of being cytotoxic and/or producing increased amounts of type-1 helper chemokines such as IFNγ and/or TNFα and/or TNFβ. When referring to an NK cell or a CD4$^+$ T cell, the term "active" includes or refers to a state of producing increased amounts of type-1 helper chemokines such as IFNγ and/or TNFα and/or TNFβ, also known as a state of being type-1-polarized. The term "inactive" refers herein to cells that do not exhibit the aforementioned "active" characteristics. Inactive cells include nave cells and memory cells. A "memory cell" is a long-lived lymphocyte that carries the antibody or receptor for a specific antigen after a first exposure to the antigen and that remains in a less than mature state until stimulated by a second exposure to the antigen at which time it mounts a more effective immune response than a cell which has not been exposed previously. In some embodiments, inactive NK cells are characterized by low surface expression of CD25 and CD69, and show low immediate cytolytic activity. In some embodiments, inactive NK cells are obtained from the subject to be treated according to the methods described herein.

The term "cancer" is used to address any neoplastic disease, and is not limited to epithelial neoplasms (surface and glandular cancers; such a squamous cancers or adenomas). The term "cancer" is used here to describe both solid tumors and hematologic malignancies, including epithelial (surface and glandular) cancers, soft tissue and bone sarcomas, angiomas, mesothelioma, melanoma, lymphomas, leukemias and myeloma.

The term "precancerous condition" includes any condition which may develop into a cancer including, but not limited to, chronic infections (including, but not limited to HIV, HPV, Hepatitis B and Hepatitis C, EBV, CMV, *M. tuberculosis*, and intracellular bacteria and parasites), as well as chronic inflammatory states, including inflammatory bowel disease (including Crohn's and ulcerative colitis), Barrett's esophagus, Ductal carcinoma in situ (CIS), cervical intraepithelial neoplasia (CIN), vulvar intraepithelial neoplasia (VIN), chronic pancreatitis, chronic hepatitis (viral and non-viral etiologies), lymphoproliferative syndromes, chronic gastritis, chronic esophagitis, chronic obstructive pulmonary disease (COPD) and globulinopathies.

The terms "cell," "cell line," and "cell culture" include progeny. It is also understood that all progeny may not be precisely identical in DNA content, due to deliberate or inadvertent mutations. Variant progeny within a population, which population has the same increased expression of CXCR4 as screened for in the originally engineered cell population, are included.

The term "chronic infection" refers herein to an infection lasting about three months or more. In some embodiments, a chronic infection is associated with the increased production of anti-inflammatory chemokines in and/or around the infected area(s). Chronic infections include, but are not limited to, infections by HIV, HPV, Hepatitis B, Hepatitis C, EBV, CMV, *M. tuberculosis*, and intracellular bacteria and parasites.

A "composition" is intended to include a combination of active agent or agents (for example, one or more active CXCR4$^+$ CD8$^+$ T cells) and another compound or composition, inert (for example, a detectable agent or label) or active, such as an adjuvant.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative." Various controls within the scope of the present invention are described in more detail below.

The term "CXCR4+" refers herein to a cell or a population of cells having surface expression of CXCR4. "CXCR4" refers herein to a C-X-C chemokine receptor type 4 polypeptide also known as fusin or CD184 (cluster of differentiation 184) that binds to CXCL12 (or stromal cell derived factor-1 (SDF-1)), and in humans, is encoded by the CXCR4 gene. In some embodiments, the CXCR4 polypeptide or polynucleotide is that identified in one or more publicly available databases as follows: HGNC: 2561, Entrez Gene: 7852, Ensembl: ENSG00000121966, OMIM: 162643, and UniProtKB: P61073. In some embodiments, the CXCR4 polypeptide comprises the sequence of SEQ ID NO:1, or a polypeptide sequence having at or greater than about 80%, at or greater than about 85%, at or greater than about 90%, at or greater than about 95%, or at or greater than about 98% homology with SEQ ID NO:1, or a polypeptide comprising a portion of SEQ ID NO:1. The CXCR4 polypeptide of SEQ ID NO:1 may represent an immature or pre-processed form of mature CXCR4, and accordingly, included herein are mature or processed portions of the CXCR4 polypeptide in SEQ ID NO:1.

The term "cytotoxic" as used herein refers to the ability to kill a target cell. A cytotoxic T cell or NK cell may kill a target cell via target cell apoptosis using one or more different mechanisms including release of one or more cytotoxins or expression of a Fas ligand. As used herein, the term "CTL" refers to a cytotoxic T cell. In some embodiments, a cytotoxic T cell or NK cell kills a tumor cell via the release of one or more cytotoxins. "Cytotoxin" includes, but is not limited to, a perforin, a granzyme and a granulysin. Currently known granzymes are Granzyme A (GZMA), Granzyme B (GZMB), Granzyme H (GZMH), Granzyme K (GZMK), and Granzyme M (GZMM).

An "effective amount" is an amount sufficient to effect beneficial or desired results. An effective amount can be administered in one or more administrations, applications or dosages.

As used herein, "gene expression" and "protein expression" refer to the process by which polynucleotides are transcribed into mRNA and the process by which the transcribed mRNA is subsequently being translated into peptides, polypeptides, or proteins, respectively. If the polynucleotide is derived from genomic DNA, expression may include splicing of the mRNA in a eukaryotic cell. "Gene overexpression" refers to the overproduction of the mRNA transcribed from the gene, at a level that is about 2.5 times higher, about 5 times higher, or about 10 times higher than the expression level detected in a control sample. "Protein overexpression" includes the overproduction of the protein product encoded by a gene at a level that is about 2.5 times higher, about 5 times higher, or about 10 times higher than the expression level detected in a control sample.

As used herein "surface expression" refers to the process by which polypeptides are translocated to the surface of a cell such that at least a portion of the polypeptide is located at the exterior of the cell surface. "Surface overexpression" includes an increase in the amount of a particular polypeptide at the exterior surface of a cell, at a level that is about 2.5 times higher, about 5 times higher, or about 10 times higher than the surface expression level detected in a control sample. In some embodiments, "surface expression" relates to the expression of a receptor that binds to a compound at the cell surface exterior, such as, for example, an interleukin receptor.

"Granzyme B" and "GZMB" are used interchangeably and refer herein to a polypeptide sequence that functions as a serine protease and can assist in the induction of apoptosis in a target cell. In some embodiments, the GZMB polypeptide or polynucleotide is that identified in one or more publicly available databases as follows: HGNC: 4709, Entrez Gene: 3002, Ensembl: ENSG00000100453, OMIM: 123910, and UniProtKB: P10144. In some embodiments, the GZMB polypeptide comprises the sequence of SEQ ID NO:2, or a polypeptide sequence having at or greater than about 80%, at or greater than about 85%, at or greater than about 90%, at or greater than about 95%, or at or greater than about 98% homology with SEQ ID NO:2, or a polypeptide comprising a portion of SEQ ID NO:2. The GZMB polypeptide of SEQ ID NO:2 may represent an immature or pre-processed form of mature GZMB, and accordingly, included herein are mature or processed portions of the GZMB polypeptide in SEQ ID NO:2.

As used herein, the term "hypoxic condition" includes hypoxia and one or more hypoxia-mimicking compounds. The term "hypoxia" refers to a partial pressure of oxygen in an atmosphere that is below about 21%. In some embodiments, the hypoxia is a partial pressure of oxygen in an atmosphere that is at or below: about 10%, about 9%, about 8%, about 7%, about 6%, about 5%, about 4%, about 3%, about 2%, or about 1%. Since the cells are typically cultured in 20-21% oxygen (control conditions), in some embodiments hypoxia is a partial pressure of oxygen in tissue cultures that is at or below: about 21%, about 20%, about 19%, about 18%, about 17%, about 16%, about 15%, about 14%, about 13%, about 12%, or about 11%. In some embodiments, the atmosphere is contained within a closed space such as a cell culture chamber. The term "hypoxia-mimicking compound" includes HIF-1a stabilizers. Hypoxia-mimicking compounds include, but are not limited to, cobalt chloride ($CoCl_2$), dimethyloxalylglycine (DMOG), desferrioxamine, o-phenanthroline, iodochlorohydroxyquinoline, and cobalt sulfate heptahydrate.

The term "identity" or "homology" shall be construed to mean the percentage of nucleotide bases or amino acid residues in the candidate sequence that are identical with the bases or residues of a corresponding sequence to which it is compared, after aligning the sequences and introducing gaps, if necessary to achieve the maximum percent identity for the entire sequence, and not considering any conservative substitutions as part of the sequence identity. Neither N- nor C-terminal extensions nor insertions shall be construed as reducing identity or homology. A polynucleotide or polynucleotide region (or a polypeptide or polypeptide region) that has a certain percentage (for example, about 80%, about 85%, about 90%, or about 95%) of "sequence homology" to another sequence means that, when aligned, that percentage of bases (or amino acids) are the same in comparing the two sequences. This alignment and the percent homology or sequence identity can be determined using software programs known in the art. In one embodiment, default parameters are used for alignment. In one embodiment a BLAST program is used with default parameters. In one embodiment, BLAST programs BLASTN and BLASTP are used with the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

"Mammal" for purposes of treatment refers to any animal classified as a mammal, including human, domestic and farm animals, nonhuman primates, and zoo, sports, or pet animals, such as dogs, horses, cats, cows, etc.

As used herein the term "naïve" refers to a fully-developed (post-thymic), yet non-activated by antigen or NK cell ligand, cell (CD4$^+$ or CD8$^+$ T cell). In some embodiments, naïve T cells are characterized by the surface expression of L-selectin (CD62L); the absence of the activation markers CD25, CD44 or CD69; and the absence of memory CD45RO isoform. In some further embodiments, naïve T cells also express functional IL-7 receptors, consisting of subunits IL-7 receptor-α, CD127, and common-γ chain, CD132. In some embodiments, naïve T cells are obtained from the subject to be treated according to the methods described herein.

As used herein, the terms "neoplastic cells," "neoplasia," "tumor cells," "tumor," "cancer," and "cancer cells" (used interchangeably) refer to cells which exhibit relatively autonomous growth, so that they exhibit an aberrant growth phenotype characterized by a significant loss of control of cell proliferation (i.e., de-regulated cell division). Tumor cells can be malignant or benign. A metastatic cell or tissue means that the cell can invade and destroy neighboring body structures.

A "pharmaceutical composition" is intended to include the combination of an active agent with a pharmaceutically acceptable carrier, inert or active, making the composition suitable for diagnostic or therapeutic use in vivo or ex vivo.

The term "pharmaceutically acceptable carrier" means a carrier or excipient that is useful in preparing a pharmaceutical composition that is generally safe and non-toxic, and includes a carrier that is acceptable for veterinary and/or human pharmaceutical use. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below. The pharmaceutical compositions also can include preservatives. A "pharmaceutically acceptable carrier" as used in the specification and claims includes both one and more than one such carrier.

The terms "pharmaceutically effective amount," "therapeutically effective amount," and "therapeutically effective dose" refer to the amount of a composition such as an active CXCR4$^+$ CD8$^+$ T cell, active CXCR4$^+$ CD4$^+$ T cell, and/or active CXCR4$^+$ NK cell composition that will elicit the biological or medical response of a tissue, system, animal, or human that is being sought by the researcher, veterinarian, medical doctor or other clinician. In some embodiments, a desired response is a treatment of a cancer. In some instances, a desired biological or medical response is achieved following administration of multiple dosages of the composition to the subject over a period of days, weeks, or years. The terms "pharmaceutically effective amount," "therapeutically effective amount," and "therapeutically effective dose" include that amount of a composition such as an active CXCR4$^+$ CD8$^+$ T cell, active CXCR4$^+$ CD4$^+$ T cell, and/or active CXCR4$^+$ NK cell composition that, when administered, is sufficient to prevent development of, or alleviate to some extent, one or more of the symptoms of the condition or disorder being treated. The therapeutically effective amount will vary depending on the composition such as the active CXCR4$^+$ CD8$^+$ T cell, active CXCR4$^+$ CD4$^+$ T cell, and/or active CXCR4$^+$ NK cell composition, the disorder or conditions and its severity, the route of administration, time of administration, rate of excretion, drug combination, judgment of the treating physician, dosage form, and the age, weight, general health, sex and/or diet of the subject to be treated. In the context of the present method, a pharmaceutically or therapeutically effective amount or dose of an active CXCR4$^+$ CD8$^+$ T cell, active CXCR4$^+$ CD4$^+$ T cell, and/or active CXCR4$^+$ NK cell composition includes an amount that is sufficient to prevent development of, suppress the growth of, or reduce the numbers of, one or more cancers or tumors. A pharmaceutically or therapeutically effective amount or dose of an active CXCR4$^+$ CD8$^+$ T cell, active CXCR4$^+$ CD4$^+$ T cell, and/or active CXCR4$^+$ NK cell composition also includes an amount that is sufficient to treat a precancerous condition or chronic infection.

The term "polypeptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

The terms "prevent," "preventing," "prevention," and grammatical variations thereof as used herein, refer to a method of partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

To "suppress" tumor growth indicates a curtailment of growth state when compared to growth without contact with an active CXCR4$^+$ CD8$^+$ T cell, active CXCR4$^+$ CD4$^+$ T cell, and/or active CXCR4$^+$ NK cell composition described herein. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage.

The terms "treat," "treating," "treatment" and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection. In some instances, the terms "treat," "treating," "treatment" and grammatical variations thereof, include partially or completely reducing the size of a solid tumor or reducing the number of solid tumors as compared with prior to treatment of the subject or as compared with the incidence of such symptom in a general or study population.

The term "type-1 polarizing condition" refers herein to a condition that, when alone or in combination with another condition, is applied to a T cell or an NK cell and causes that cell to predominantly produce a type-1 or T1 pattern of chemokines including one or more of interferon-γ (IFN-γ), TNFα, lymphotoxin plus IL-3, and GM-CSF with or without IL-2. Type-1 polarizing conditions include, but are not limited to, interleukin 12 receptor stimulation, IFN-γ receptor stimulation, IFN-α/βreceptor (type I IFN receptor) stimulation, interleukin 27 receptor stimulation, interleukin 18 receptor stimulation, interleukin 15 receptor stimulation, CD3 stimulation, CD28 stimulation, CD40 stimulation, and (in the case of T cells) T cell receptor stimulation.

The terms "Th1" and "Th1-type-CD4$^+$ T cell" are used interchangeably herein and refer to T cells that comprise a surface expressed CD4 molecule and 1) increased- or over-expression of a T-bet and/or 2) increased production of IFN-γ and/or TNF-β. The CD4 molecule is specific for MHC Class II molecules. Therefore, a CD4$^+$ T cell specifically binds to a target cell having surface expression of MHC Class II bound to an antigen (the target cell commonly referred to as an "antigen presenting cell" or "APC"). Once activated, a Th1-type-CD4$^+$ T cell may produce chemokines such as IFN-γ and TNF-β to activate effector cells such as macrophages and cytotoxic CD8$^+$ T cells.

The term "T-bet" refers to a polynucleotide or polypeptide sequence also known as T-Box 21 or TBX21 that functions as a transcription factor involved in the expression of IFN-γ. In some embodiments, the T-bet polypeptide or polynucleotide is that identified in one or more publicly available databases as follows: HGNC: 11599, Entrez Gene: 30009, Ensembl: ENSG00000073861, OMIM: 604895, UniProtKB: Q9UL17.

DETAILED DESCRIPTION

Provided herein are active CXCR4$^+$ CD8$^+$ T cells, active CXCR4$^+$ CD4$^+$ T cells and active CXCR4$^+$ NK cells and populations of those cells, methods for making active CXCR4$^+$ CD8$^+$ T cells, active CXCR4$^+$ CD4$^+$ T cells and active CXCR4$^+$ NK cells and populations of those cells, and methods for using active CXCR4$^+$ CD8$^+$ T cells, active CXCR4$^+$ CD4$^+$ T cells and active CXCR4$^+$ NK cells and populations of those cells for the treatment of cancer. It is a surprising finding of the present invention that active CD8$^+$ T cells, active Th1-type-CD4$^+$ T cells and active NK cells may be created that have increased surface expression of CXCR4. It was previously believed that the pattern of development of T cell effector functions (cytotoxic/type-1 versus non-cytotoxic/regulatory) determines the pattern of chemokine receptor expression and migratory pattern of the resulting T cells, such that cytotoxicity and reduced CXCR4 surface expression could not be uncoupled. Active T cells and NK cells having the combination of cytotoxicity and increased CXCR4 surface expression may be used for treatment of cancer, and in some embodiments, solid tumors, as the active CXCR4$^+$ T cells and NK cells migrate toward CXCL12 producing cancers and effect tumor cell apoptosis.

Accordingly, provided herein are active CD8$^+$ T cells having cytotoxicity and comprising increased CXCR4 surface expression as compared to a control. Also provided herein are active CD8$^+$ T cells producing high amounts of type-1 helper chemokines such as IFNγ and/or TNFα and/or TNFβ and comprising increased CXCR4 surface expression as compared to a control. Further provided herein are active CD8$^+$ T cells having cytotoxicity, producing high amounts of type-1 helper chemokines such as IFNγ and/or TNFα and/or TNFβ, and comprising increased CXCR4 surface expression as compared to a control. The CD8$^+$ T cells may be T cells of any origin, and in some embodiments, are of mammalian or human origin. As used herein, the term "T cell" is synonymous with "T lymphocyte" and refers to an immune cell comprising a surface expressed T cell antigen receptor (TCR), which receptor binds to an antigen bound to a major histocompatability complex (MHC). It should be understood that the terms "T cell antigen receptor" and "TCR" include any surface expressed structure that binds to an antigen bound to a MHC, and includes artificial or engineered TCRs such as chimeric antigen receptors (CARs). Accordingly T cells included within the present disclosure are recombinant TCR- or CAR-modified cells, ex vivo-expanded tumor infiltrating lymphocytes (TILs), in vitro-sensitized or activated blood- or tumor-isolated T cells, and antibody-armed T cells.

As used herein, and as understood by those of skill in the art, a "CD8$^+$ T cell" is a T cell that comprises a surface expressed CD8 molecule. The CD8 molecule is specific for MHC Class I molecules. Therefore, a CD8$^+$ T cell specifically binds to a target cell having surface expression of MHC Class I bound to an antigen (the target cell commonly referred to as an "antigen presenting cell" or "APC"). Once activated, a CD8$^+$ T cell may cause apoptosis of the APC and thus be cytotoxic to the APC.

Also provided herein are active NK cells having cytotoxicity or increased production of helper chemokines and comprising increased CXCR4 surface expression as compared to a control. The NK cells may be of any origin, and in some embodiments, are of mammalian or human origin. As used herein, the term "NK cell" is synonymous with "natural killer cell." NK cells do not express TCR or the Pan T marker CD3, but usually express the surface markers CD16 (FcγRIII) and CD56 in humans. Once activated, NK cells may become cytotoxic lymphocytes that may cause apoptosis of a target cell via mechanisms similar to those of activated CD8$^+$ T cells.

Further provided herein are active Th1-type-CD4$^+$ T cells comprising increased CXCR4 surface expression as compared to a control. The Th1-type-CD4$^+$ T cells may be T cells of any origin, and in some embodiments, are of mammalian or human origin. As used herein, and as understood by those of skill in the art, the term "Th1-type-CD4$^+$ T cell" refers to T cells that comprise a surface expressed CD4 molecule and that have increased production of helper chemokines such as IFN-γ and/or TNF-β. The CD4 molecule is specific for MHC Class II molecules. Therefore, a CD4$^+$ T cell specifically binds to a target cell having surface expression of MHC Class II bound to an antigen (the target cell commonly referred to as an "antigen presenting cell" or "APC"). Once activated, a Th1-type-CD4$^+$ T cell may produce chemokines such as IFN-γ and TNF-β to activate effector cells such as macrophages and cytotoxic CD8$^+$ T cells.

In some embodiments, the CXCR4 surface expression on the active CD8$^+$ T cells, active Th1-type-CD4$^+$ T cells or active NK cells is at least about 5% higher, at least about 10% higher, at least about 20% higher, at least about 30% higher, at least about 40% higher, at least about 50% higher, at least about 100% higher, or at least about 500% higher than a control CD8$^+$ T cell, Th1-type-CD4$^+$ T cell, or a control NK cell, respectively. In some embodiments, the CXCR4 surface expression is increased in a population of active CD8$^+$ T cells, active Th1-type-CD4$^+$ T cells or active NK cells by at least about 5% higher, at least about 10% higher, at least about 20% higher, at least about 30% higher, at least about 40% higher, at least about 50% higher, at least about 100% higher, or at least about 500% higher as compared to a control CD8$^+$ T cell population, a control Th1-type-CD4$^+$ T cell population, or a control NK cell population, respectively. The term "higher" as used herein refers to either the percentage of CXCR4-positive cells or the mean level of CXCR4 expression on the population of cells, or both. Control CD8$^+$ T cells/cell populations, Th1-type-CD4$^+$ T cell populations, and NK cells/cell populations are those cells/cell populations that have not been exposed to one or more of activation, a hypoxic condition, and IL-12. In some embodiments, increased CXCR4 expression is achieved in a CD8$^+$ T cell, Th1-type-CD4$^+$ T or NK cell without the introduction of additional and/or exogenous polynucleotide sequences, such as CXCR4 encoding or regulatory polynucleotide sequences, into the CD8$^+$ T cell, CD4+ T cell or NK cell. In these embodiments, the CXCR4 is "non-recombinant" or "non-genetically engineered."

As mentioned above, the term "active" includes being cytotoxic. The terms "cytotoxic" and "cytotoxicity" refer to the ability of the T cell or NK cell to kill a target cell. A cytotoxic T cell or NK cell may kill a target cell via target cell apoptosis using one or more different mechanisms including release of one or more cytotoxins or expression of a Fas ligand. In some embodiments, a cytotoxic T cell or NK cell kills a tumor cell via the release of one or more cytotoxins. "Cytotoxin" includes, but is not limited to, a perforin, a granzyme and a granulysin. Currently known granzymes are Granzyme A (GZMA), Granzyme B (GZMB), Granzyme H (GZMH), Granzyme K (GZMK), and Granzyme M (GZMM).

The cytotoxicity of a T cell or an NK cell may be determined and/or measured via any method known to one of ordinary skill in the art. In some embodiments, apoptosis of the target cell is determined by measuring caspase activation in the target cell. In some embodiments, caspase activation is determined by the measurement of caspase-3 activation. In other embodiments, apoptosis of the target cell is determined by intracellular radiolabeling the target cell with Chromium ($^{51}$Cr) and measuring release of the Chromium from the target cell. In still other or further embodiments, cytotoxicity may be indicated by increased GZMB protein expression as compared to a control cell (increased levels of expression in individual cells and/or increased proportions of positive cells).

The term "active" also includes a state of producing increased amounts of helper cytokines such as IFNγ, TNFα and/or TNFβ. Increased production of such as IFNγ, TNFα and/or TNFβ by an NK cell or Th1-type-CD4$^+$ T cell may be determined and/or measured via any method known to one of ordinary skill in the art.

Although the present disclosure includes active CXCR4$^+$ CD8$^+$ T cells, active CXCR4$^+$ Th1-type-CD4$^+$ T cells, and active CXCR4$^+$ NK cells having increased cytotoxicity or increased production of IFNγ, TNFα and/or TNFβ as compared to control CXCR4$^-$ CD8$^+$ T cells, control CXCR4$^-$ CD4$^+$ T cells, and control CXCR4$^-$ NK cells, respectively, it should be understood that the present disclosure also includes active CXCR4$^+$ CD8$^+$ T cells, active CXCR4$^+$ CD4$^+$ T cells and active CXCR4$^+$ NK cells having the same or less cytotoxicity (or production of IFNγ) as compared to control CXCR4$^-$ CD8$^+$ T cells, control CXCR4$^-$ CD4$^+$ T cells, and control CXCR4$^-$ NK cells, respectively.

In some embodiments, the active CXCR4$^+$ CD8$^+$ T cells, active CXCR4$^+$ Th1-type-CD4$^+$ T cells, and active CXCR4$^+$ NK cells are made via a non-recombinant method. The term "non-recombinant method" refers herein to a method wherein at least some, and in some embodiments, all, increased CXCR4 surface expression is achieved without the introduction additional and/or exogenous polynucleotide sequences, such as CXCR4 encoding or regulatory polynucleotide sequences, into the CD8$^+$ T cell, CD4$^+$ T cell, or NK cell.

In some embodiments, the method of making active CXCR4$^+$ CD8$^+$ T cells, active CXCR4$^+$ Th1-type-CD4$^+$ T cells or active CXCR4$^+$ NK cells comprises the steps of 1) providing an inactive CD8$^+$ T cell, inactive CD4$^+$ T cell, or an inactive NK cell, 2) exposing the CD8$^+$ T cell, CD4$^+$ T cell, or the NK cell to one or more type-1 polarizing conditions, and 3) exposing the CD8$^+$ T cell, CD4$^+$ T cell, or the NK cell to a hypoxic condition. In some embodiments, step 3) may be performed simultaneously, prior to, or after step 2). In some embodiments, the inactive cell is a nave cell. In other embodiments, the inactive cell is a memory cell. Accordingly, included herein are active CXCR4$^+$ CD8$^+$ T cells, active CXCR4$^+$ NK cells, and active CXCR4$^+$ Th1-type-CD4$^+$ T cells made by the methods described herein.

In still other embodiments, the method of making active CXCR4$^+$ CD8$^+$ T cells, active CXCR4$^+$ Th1-type-CD4$^+$ T cells or active CXCR4$^+$ NK cells comprises the steps of 1) providing an active CD8$^+$ T cell, CD4$^+$ T cell, or NK cell, and 2) exposing the CD8$^+$ T cell, CD4$^+$ T cell, or the NK cell to one or more hypoxic conditions. Accordingly, provided herein is a method of making an active CXCR4$^+$ CD8$^+$ T cell or cell population comprising providing an active CD8$^+$ T cell or cell population and exposing the T cell or cell population to one or more hypoxic conditions. Also provided herein is a method of making an active CXCR4$^+$ Th1-type-CD4$^+$ T cell or cell population comprising providing an active CD4$^+$ T cell or cell population and exposing the T cell or cell population to one or more hypoxic conditions. Further provided herein is a method of making an active CXCR4$^+$ NK cell or cell population comprising providing an active NK cell or cell population and exposing the NK cell or cell population to one or more hypoxic conditions.

As discussed above, the term "type-1 polarizing condition" refers herein to a condition that, when alone or in combination with another condition, is applied to a T cell or an NK cell, causes that cell to predominantly produce a type-1 or T1 pattern of chemokines including one or more of interferon-γ (IFN-γ), TNFα, lymphotoxin plus IL-3, and GM-CSF with or without IL-2. Type-1 polarizing conditions include, but are not limited to, interleukin 12 receptor stimulation, IFN-γ receptor stimulation, IFN-α/β receptor (type I IFN receptor) stimulation, interleukin 27 receptor stimulation, interleukin 18 receptor stimulation, interleukin 15 receptor stimulation CD3 stimulation, CD28 stimulation, CD40 stimulation, and T cell receptor stimulation. It should be understood that "type-1 polarizing condition" includes a type-1 polarized antigen presenting cell loaded (or pulsed) with antigen and CD40 stimulation. One such antigen presenting cell is a dendritic cell. A dendritic cell may be type-1 polarized by exposing the cell to lipopolysaccharide (LPS) and IFN-γ. In some embodiments, the CD8$^+$ T cell, CD4$^+$ cell, or NK cell is exposed to the type-1 polarizing condition for about one to ten days, about two to nine days, about three to eight days, about four to seven days, or about six days.

In some embodiments, an active CXCR4$^+$ CD8$^+$ T cell is made by a method comprising providing a naïve or memory CD8$^+$ T cell, exposing the CD8$^+$ T cell to IL-12 (or IL-12-producing cell, or an alternative type-1-polarizing factor), and CD3 stimulation, and CD28 stimulation, and 3) exposing the T cell to a hypoxic condition. In some embodiments, an active CXCR4$^+$ Th1-type-CD4$^+$ T cell is made by a method comprising providing a naïve or memory CD4$^+$ T cell, exposing the CD4$^+$ T cell to IL-12 (or IL-12-producing cell, or alternative type-1-polarizing factor), CD3 stimulation, and CD28 stimulation, and 3) exposing the T cell to a hypoxic condition. In some embodiments, an active CXCR4$^+$ NK cell is made by a method comprising providing a naïve NK cell, exposing the NK cell to IL-12 (or IL-12-producing cell, or alternative type-1-polarizing factor), and 3) exposing the NK cell to a hypoxic condition.

As noted above, the term "hypoxic condition" includes hypoxia and hypoxia-mimicking compounds. The term "hypoxia" refers to a partial pressure of oxygen in an atmosphere that is below about 21%. In some embodiments, the hypoxia is a partial pressure of oxygen in an atmosphere that is at or below about 10%, at or below about 9%, at or below about 8%, at or below about 7%, at or below about 6%, at or below about 5%, at or below about 4%, at or below about 3%, at or below about 2%, or at or below about 1%. Since the cells are typically cultured in 20-21% oxygen (control conditions), in some embodiments hypoxia is a partial pressure of oxygen in tissue cultures that is below about 21%, below about 20%, below about 19%, below about 18%, below about 17%, below about 16%, below about 15%, below about 14%, below about 13%, below about 12%, or below about 11%, or below about 10%, or below about 4%, or below about 2%, or below about 1%. In some embodiments, the atmosphere is contained within a closed space such as a cell culture chamber. The term "hypoxia-mimicking compound" includes, but is not limited to, HIF-1α stabilizers such as cobalt chloride (CoCl$_2$), dimethyloxalylglycine (DMOG), o-phenanthroline, iodochlorohydroxyquinoline, and cobalt sulfate heptahydrate. In some embodiments, the CD8$^+$ T cell, CD4$^+$ T cell, or NK cell is exposed to the hypoxic condition for less than one day, about one to about six days, about two to about five days, or about three days.

Accordingly, in some embodiments, an active CXCR4$^+$ CD8$^+$ T cell is made by a method comprising 1) providing a naïve or memory CD8$^+$ T cell, 2) exposing the CD8$^+$ T cell to IL-12, T cell receptor/CD3 complex stimulation (cognate antigen or alternative ligand, such as anti-CD3 ligand, and costimulatory signals, including CD28 stimulation, and/or effector-cell-promoting signals such as IL-12, and 3) exposing the T cell to hypoxia, wherein the hypoxia is a partial pressure of oxygen in an atmosphere that is at or below about 21%. In other embodiments, an active CXCR4$^+$ CD8$^+$ T cell is made by a method comprising 1) providing a naïve or memory CD8$^+$ T cell, 2) exposing the CD8$^+$ T cell to IL-12, CD3 stimulation, and CD28 stimulation, and 3) exposing the T cell to one or more HIF-1α stabilizers. In one embodiment, the HIF-1α stabilizer is DMOG. It should be understood that the present invention encompasses methods wherein the CD8$^+$ T cell is exposed to a hypoxic condition (step 3) before it is stimulated (step 2).

In other embodiments, an active CXCR4$^+$ Th1-type-CD4$^+$ T cell is made by a method comprising 1) providing a naïve or memory CD4$^+$ T cell, 2) exposing the CD4$^+$ T cell to IL-12, CD3 stimulation, and CD28 stimulation, and 3) exposing the T cell to hypoxia, wherein the hypoxia is a partial pressure of oxygen in an atmosphere that is at or below about 21%. In other embodiments, an active CXCR4$^+$ Th1-type-CD4$^+$ T cell is made by a method comprising 1) providing a naïve or memory CD4$^+$ T cell, 2) exposing the CD4$^+$ T cell to IL-12, CD3 stimulation, and CD28 stimulation, and 3) exposing the T cell to one or more HIF-1α stabilizers. In one embodiment, the HIF-1α stabilizer is DMOG. It should be understood that the present invention encompasses methods wherein the CD4$^+$ T cell is exposed to a hypoxic condition (step 3) before it is stimulated (step 2).

In other embodiments, an active CXCR4$^+$ NK cell is made by a method comprising 1) providing a naïve or memory NK cell, 2) exposing the NK cell to IL-12, and 3) exposing the NK cell to hypoxia, wherein the hypoxia is a partial pressure of oxygen in an atmosphere that is at or below about 21%. In other embodiments, an active CXCR4$^+$ NK cell is made by a method comprising 1) providing a naïve or memory NK cell, 2) exposing the NK cell to IL-12, and 3) exposing the NK cell to one or more HIF-1α stabilizers. In one embodiment, the HIF-1α stabilizer is DMOG. It should be understood that the present invention encompasses methods wherein the NK cell is exposed to a hypoxic condition (step 3) before it is stimulated (step 2).

Also provided herein are methods of using the active CXCR4$^+$ CD8$^+$ T cells, active CXCR4$^+$ Th1-type-CD4$^+$ T cell and/or active CXCR4$^+$ NK cells for the treatment of a cancer. Provided herein is a method of treating a cancer in a subject comprising administering to the subject a pharmaceutically effective amount of an active CXCR4$^+$ CD8$^+$ T cell composition, an active CXCR4$^+$ Th1-type-CD4$^+$ T cell composition, and/or an active CXCR4$^+$ NK cell composition, wherein the active CXCR4$^+$ CD8$^+$ T cell, active CXCR4$^+$ Th1-type-CD4$^+$ T cell, and/or active CXCR4$^+$ NK cell is as described herein. In some embodiments, the active CXCR4$^+$ CD8$^+$ T cell composition comprises a population of CXCR4$^+$ CD8$^+$ T cells having increased surface expression of CXCR4 as compared to a control population of CD8$^+$ T cells. In other or further embodiments, the active CXCR4$^+$ Th1-type-CD4$^+$ T cell composition comprises a population of CXCR4$^+$ Th1-type-CD4$^+$ T cells having increased surface expression of CXCR4 as compared to a control population of CXCR4$^+$ Th1-type-CD4$^+$ T cells. In other or further embodiments, the active CXCR4$^+$ NK cell composition comprises a population of CXCR4$^+$ NK cells having increased surface expression of CXCR4 as compared to a control population of NK cells. Accordingly, further provided is a pharmaceutical composition comprising an active CXCR4$^+$ CD8$^+$ T cell composition, an active CXCR4$^+$ Th1-type-CD4$^+$ T cell composition, and/or an active CXCR4$^+$ NK cell composition as described herein.

In some embodiments of the method of treatment, the cancer is a tumor. A tumor includes a carcinoma, a sarcoma, lymphoma and leukemia. Tumors can arise in any tissue including, but not limited to, breast, head and neck, lung, airways, prostate, colon, brain, cervix, uterus, ovaries, fallopian tubes, pancreas, esophagus, stomach, gastrointestinal tract, genitourinary tract, skin, liver, kidney, bone, soft connective tissue, central and peripheral nervous system and endocrine and exocrine tissues. In some embodiments, the cancer is selected from the group consisting of colorectal cancer, ovarian cancer, breast cancer, prostate cancer, and multiple myeloma. In some embodiments, the tumor is malignant. In some embodiments, the tumor is solid. The subject of treatment according to the methods described herein may be any animal, mammal, warm-blooded mammal or human. In one embodiment, the subject of treatment is a human. Accordingly, provided herein is a method of treating a cancer in a subject comprising administering to the subject a pharmaceutically effective amount of an active $CXCR4^+$ $CD8^+$ T cell, an active $CXCR4^+$ Th1-type-$CD4^+$ T cell and/or an active $CXCR4^+$ NK cell comprising an increased surface expression of a CXCR4 as compared to a control $CD8^+$ T cell, control $CD4^+$ T cell or a control NK cell, respectively.

The present invention provides a tumor therapeutic that is reliable in vivo due its use of already existing in vivo conditions such as CXCL12 expression by target tumors. More specifically, a tumor microenvironment (TME) is typically enriched in CCL22, CXCL1, CXCL2, CXCL8, and CXCL12. These chemokines are widely known to attract the CCR4-, CXCR1-, CXCR2- and CXCR4-expressing MDSCs and $T_{reg}$ cells, which promote tumor growth by protecting tumors from immune elimination and promoting tumor vascularization. Yet, for the first time, the present invention provides immune cells having both CXCR4 expression (or overexpression) and an active and tumor treating phenotype. The data herein demonstrate stability of this active $CXCR4^+$ hybrid phenotype in $CD8^+$ T cells, Th1-type-$CD4^+$ T cells and NK cells after withdrawal of the CXCR4-inducing factors such as a combination of hypoxia or hypoxia mimics, with IL-12, or DC1 activation. Since overproduction chemokines such as CXCL12 is an intrinsic feature of multiple tumor types and is used to sustain tumor growth in vivo, and since intratumoral infiltration of type-1 immune cells into tumors has been extensively demonstrate to be associated with improved outcomes of cancer patients receiving standard care and with improved effectiveness of cancer immunotherapy, the present invention is a reliable therapeutic for treatment of tumors in vivo.

Further provided herein are methods of using the active $CXCR4^+$ $CD8^+$ T cells, active $CXCR4^+$ Th1-type-$CD4^+$ T cells and/or active $CXCR4^+$ NK cells for the treatment of a precancerous condition or chronic infection. The term "precancerous condition" includes any condition which may develop into a cancer, including chronic infections (including, but not limited to, those mediated by HIV, HPV, Hepatitis B, Hepatitis C, EBV, CMV, *M. tuberculosis*, and intracellular bacteria and parasites), as well as chronic inflammatory states, including inflammatory bowel disease (including Crohn's and ulcerative colitis), Barrett's esophagus, Ductal carcinoma in situ (CIS), cervical intraepithelial neoplasia (CIN), vulvar intraepithelial neoplasia (VIN), chronic pancreatitis, chronic hepatitis (viral and non-viral etiologies), lymphoproliferative syndromes, chronic gastritis, chronic esophagitis, chronic obstructive pulmonary disease (COPD) and globulinopathies.

Accordingly, provided herein is a method of treating a precancerous condition or chronic infection in a subject comprising administering to the subject a pharmaceutically effective amount of an active $CXCR4^+$ $CD8^+$ T cell composition, an active $CXCR4^+$ Th1-type-$CD4^+$ T cell composition, and/or an active $CXCR4^+$ NK cell composition, wherein the active $CXCR4^+$ $CD8^+$ T cell, active $CXCR4^+$ Th1-type-$CD4^+$ T cell, and/or active $CXCR4^+$ NK cell is as described herein. In some embodiments, the active $CXCR4^+$ $CD8^+$ T cell composition comprises a population of $CXCR4^+$ $CD8^+$ T cells having increased surface expression of CXCR4 as compared to a control population of $CD8^+$ T cells. In other or further embodiments, the active $CXCR4^+$ Th1-type-$CD4^+$ T cell composition comprises a population of $CXCR4^+$ Th1-type-$CD4^+$ T cells having increased surface expression of CXCR4 as compared to a control population of $CXCR4^+$ Th1-type-$CD4^+$ T cells. In other or further embodiments, the active $CXCR4^+$ NK cell composition comprises a population of $CXCR4^+$ NK cells having increased surface expression of CXCR4 as compared to a control population of NK cells.

Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer or precancerous condition including, but not limited to, a chronic infection. Prophylactic administration can occur for several days to years prior to the manifestation of symptoms of cancer. In some instances, the terms "treat," "treating," "treatment" and grammatical variations thereof, include partially or completely reducing the size of a tumor, reducing the number of tumors, and reducing the spread or incidence of a cancer as compared with prior to treatment of the subject or as compared with the incidence of such symptom in a general or study population. Accordingly, the methods of treatment may comprise adoptive cell therapies (ACT) or vaccination therapies.

The present disclosure describes a unique platform of inducing active $CXCR4^+$ $CD8^+$ T cells, active $CXCR4^+$ Th1-type-$CD4^+$ T cells, and active $CXCR4^+$ NK cells capable of migrating to multiple tumors and eliminating them. This platform has direct implications for adoptive T cell therapies of cancer, and is possible due to the novel and unexpected discovery described herein that hypoxia and hypoxia-associated signals can break the tight association between cytokine profile/effector functions of developing T cells/NK cells and their chemokine receptor expression, without the need for genetic manipulation of T cells/NK cells. The resulting cells show a unique combination of effector and tumor-migratory phenotype, which was previously impossible in normal physiological conditions.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes.

EXAMPLES

Example 1

Materials and Methods

Taqman Analysis of mRNA Expression in Tumor

Four (4) mm punch biopsies of tumor tissues were placed in lysing Matrix E tubes (MP Biologicals, Solon, Ohio) containing RLT buffer (RNeasy kit, Qiagen, Valencia, Calif.), and agitated using a FP120 homogenizer (MP Biologicals). Debris-free supernatant from the lysis matrix tubes were transferred into new tubes and total RNA was extracted using the RNeasy kit. One (1) µg of RNA extracted using this method was used for cDNA synthesis and 25-50 ng of subsequent cDNA was used to perform mRNA expression analysis by Taqman analysis on Step One Plus system (Applied Biosystems). All primers used for the analysis were standard primers purchased from Applied Biosystems.

Confocal Microscopy Analysis of Tumor Sections

Four (4) mm tumor punches, either untreated or treated, were embedded in OCT medium containing cryomolds and immediately frozen in 2-methyl-butane. Six (6) µm frozen sections of the tissues were made using the cryostat and layered on SUPERFROST™ plus slides (Thermo Scientific, Rockford, Ill.). The slides were incubated in 4% paraformaldehyde for 15 minutes, washed and blocked in for 60 minutes at room temperature (RT). The slides were then stained for 3 hours at RT with antibodies for CXCL12 (ab18919, Abcam), FIB (TE-7, Millipore), CD45 (Biolegend) and CD326 (Biolegend). The slides were washed 3 times with 1×PBS and incubated with secondary antibodies anti rabbit-Alexa 647, anti-mouse-Alexa 488 (Cell signal, Danvers, Mass.) and anti-goat-Alexa 488 (Invitrogen, Carlsbad, Calif.) for 30 minutes at RT. The slides were washed 3 times with 1×PBS and once with high salt PBS. Cover slips were mounted on the sections using prolong gold anti-fade solution (Invitrogen). Confocal analyses of stained slides were performed using a LEICA TCS SL DMRE Microsystems. For quantifying cells showing positive staining, photographs were taken of 10 different fields at 63× magnification for tumor tissue sections in untreated and treated conditions and cells positive in the photographs were marked and counted by Image pro software and cell counts from 10 images were totaled and averaged.

Isolation and Analysis of Tumor Infiltrating $CD8^+$ T Cells

Tumors were minced into small pieces with scalpel, added to a 50 ml tube and digested with reagents from a tumor dissociation kit (Miltenyi Biotech) for 1 hour, then digested tissue was passed over mesh to make a single cell suspension. The single cell suspension washed twice in 1×PBS, the cell pellet was re-suspended in 60% percol, over layered with 45% and 30% percol and spun at 3200 RPM for 30 minutes. Lymphocytes typically at 60% and 45% interphase were collected and stained for CD8 and chemokine receptors.

DC Culture

For culturing dendritic cells, monocytes were cultured in IMDM+10% FBS with GM-CSF (1000 u/ml)+IL4 (1000 u/ml) for 6 days, with half media replaced on day 3 with fresh media with GMCSF+IL4. On day 6, the cells were matured into type 1 polarized DC by adding LPS (250 ng/ml) and IFNγ (1000 u/ml) or type 2 polarized DC by adding $PGE_2$ (1 µM) for 24 hours. Both DCs were harvested, either pulsed with SEB (1 ng/ml) or MUC1 peptide (10 µg/ml), to be used for T cell cultured or co-cultured with J558 mouse myeloma cells in a 1:1 ratio (50000:50000 cells) for another 24 hours. IL-12 levels in the supernatants were then analyzed by ELISA.

Ex Vivo Induction of CTL Cells

For CTL generation by CD3/CD28 stimulation, $10^5$ naïve $CD8^+$ T cells were activated with 5 µl of CD3/CD28 microbeads (Dynal) in the absence or presence of IL-12 (5 ng/ml) for 6 days, then on the 6th day they were exposed or not exposed to 50 µM $CoCl_2$, 100 µM DMOG or 1% hypoxia (H35 Hypoxystation, Don Whitley) for another 3 days. The cells were then harvested, analyzed for CXCR4, GZMB (FOXP3 buffer set was used to permeabilize the cells and the cells were then stained with GZMB (GB11) and CXCR4 (12G5) antibodies) or analyzed for migration towards CXCL12. For CTL generation with DCs, $10^5$ naïve $CD8^+$ T cells were activated with 20,000 of either LPS+IFNγ or LPS+$PGE_2$ matured DCs, along with 20,000 J558 (for CD40 ligation) for 6 days and were similarly exposed or non-exposed for 3 additional days to 50 µM $CoCl_2$, 100 µM DMOG or 1% hypoxia, culminating in functional and migratory phenotype analysis of 9th day cells.

Ex Vivo Induction of Active $CXCR4^+$ Th1-Type-$CD4^+$ T Cells

For active $CXCR4^+$ Th1-type-$CD4^+$ T cell by CD3/CD28 stimulation, $10^5$ naïve $CD4^+$ T cells were activated with 5 µl of CD3/CD28 microbeads (Dynal) in the absence or presence of IL-12 (5 ng/ml) for 6 days, then on the 6th day they were exposed or not exposed to 50 µM $CoCl_2$, 100 µM DMOG or 1% hypoxia (H35 Hypoxystation, Don Whitley) for another 3 days. The cells were then harvested, analyzed for CXCR4 and IFNγ or analyzed for migration towards CXCL12. For CXCR4 detection, a FOXP3 buffer set was used to permeabilize the cells and the cells were then stained for CXCR4 using 12G5 antibody. For active $CXCR4^+$ Th1-type-$CD4^+$ T cell generation with DCs, $10^5$ naïve $CD4^+$ T cells were activated with 20,000 of either LPS+IFNγ or LPS+$PGE_2$ matured DCs, along with 20,000 J558 (for CD40 ligation) for 6 days and were similarly exposed or non-exposed for 3 additional days to 50 µM $CoCl_2$, 100 µM DMOG or 1% hypoxia, culminating in functional and migratory phenotype analysis of 9th day cells.

Chemotaxis

Chemotaxis assays were performed in 24 transwell plates with 5 µm pore size polycarbonate filter (Corning Inc., Corning, N.Y.). The lower chamber was filled with 500 µL of recombinant CXCL12 or tumor supernatants and $2\times10^5$ cells of normoxia or hypoxia/DMOG/$CoCl_2$ cultured $CD8^+$ Teff cells in 200 µL were added in the upper chamber and incubated for 3 hours at 37° C. Migrated cells were harvested from lower chambers and stained for GZMB, and percent of $GZMB^+$ cells and their cell count was performed by counting cells in a 100 µl volume limited run on an Accuri C6 machine.

Ex Vivo Tumor Explants Culture

Using a 4 mm biopsy puncher, relatively uniform 4 mm cubes (weight averages from 8.7 to 9.2 mg) of tumor or marginal tissue were made. The samples were then washed in RPMI with 5× concentrated antibiotics. Depending on tumor size and on the number of biopsy cubes that were generated, they were assorted as 12 cubes/well, 6 cubes/well or 3 cubes/wells in 6 well, 12 well or 24 well plates, respectively, cultured in IMDM/10% FBS, and left either untreated or in the presence of the indicated factors (IL-12, hypoxia, hypoxia mimics) for 24-48 hours. Culture supernatants were harvested at 24-48 hours for ELISA and for use in chemotaxis assays with effector cells generated in normoxia or hypoxia/Hypoxia mimetics.

$^{51}$Cr Release Assay

For $^{51}$Cr release assays, target cells-JY1 pulsed with target antigen SEB were labelled with 1 microCurie of $^{51}$Cr for 1 hour, washed 3 times, added to CD8$^+$ T cells in a ratio of 1:20, 1:10, 1:5, or 1:2.5, in a 96 well U bottom plate, spun down at 1000 rpm and incubated for 5 hours at 37° C. For spontaneous $^{51}$Cr release, target cells were left alone without incubation with cytotoxic CD8$^+$ T cells and for maximum release target cells were lysed by 1% triton-x-100. After 5 hours of incubation, the amount of Cr released from the target cells was measured by scintillation counter.

Activated Caspase-3 Assay

Cytotoxic CD8$^+$ T cells generated by various conditions were incubated with SEB pulsed target cells JY-1 cells in ratio 1:10 for 4 hours at 37° C. After incubation, cells were harvested and Stained for activated Caspase-3 and CD33 (JY-1 cell marker).

Example 2

Figure 1A:
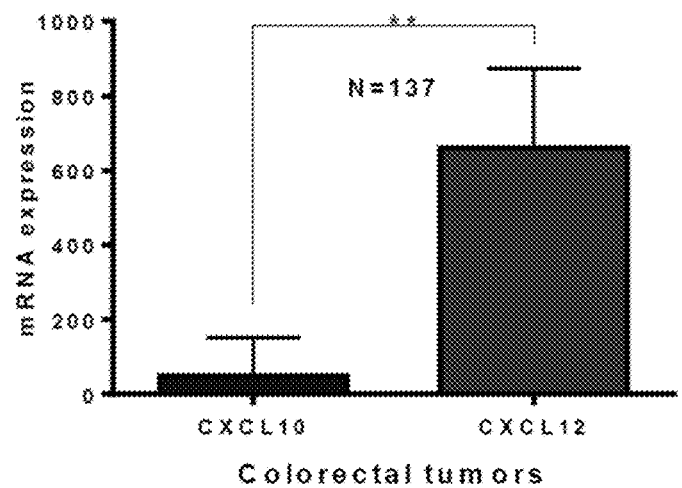
FIG. 1 (A-C) shows that colorectal tumors have prevalent high expression of CXCL12, with EPCAM positive tumor cells being major CXCL12 producers. (A) mRNA expression of CXCL10 and CXCL12 in colorectal tumors from 137 patients, as analyzed by Taqman. Data represents mean+ S.E of CXCL10 and CXCL12 mRNA expression in 137 patient tumors (B) Confocal images of CXCL12 and CD326 (EP-CAM) staining in 4 representative patient tumors. (C) CXCR4 and CXCR3 expression in $CD8^+$ T cells of the lymphocyte fraction obtained from tumors by digestion and differential percol centrifugation. Data shown is from 2 different patients.
Figure 1B:
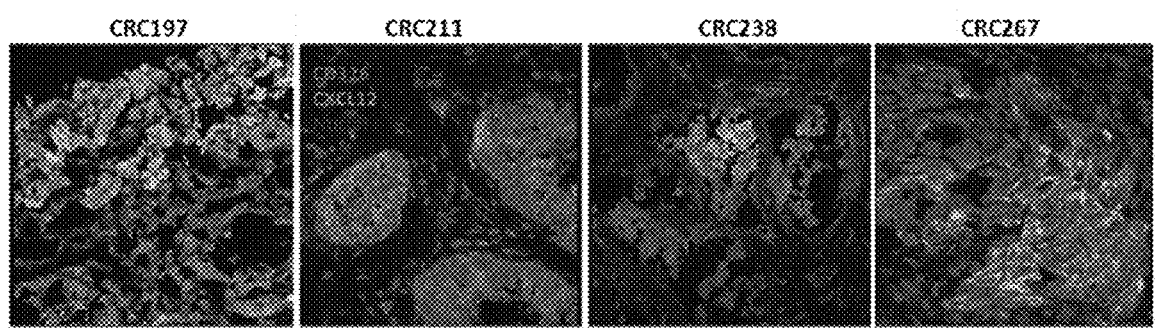
Figure 1C:
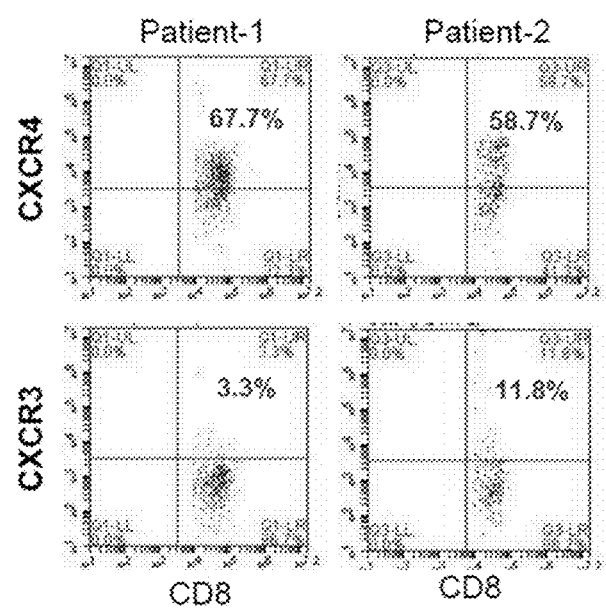

Uniform Expression of CXCL12 in Colorectal Tumors and Expression of High Levels of CXCR4 on Tumor-Infiltrating CD8$^+$ T Cells In order to identify the chemokine(s) uniformly expressed in cancer, RNA (Taqman) analysis of tumors from 137 patients was performed. The results revealed a unique pattern of spontaneous CXCL12 expression, which was spontaneously expressed at high levels in colorectal cancer tissues from 137 patients, in sharp contrast to the effector T cell attracting chemokine CXCL10, which was either absent or expressed only at marginal levels (FIG. 1A). Confocal analysis revealed that both CD326 (EP-CAM) negative (non-tumor) and positive (tumor) cells make CXCL12 (FIG. 1B). Moreover CD8$^+$ tumor infiltrating lymphocytes (TILs) isolated from tumors, showed high expression of CXCR4, rather than CXCR3, indicating that CXCR4 can drive the attraction of immune cells, including CD8$^+$ T cells (non-cytotoxic; data not shown), to cancer tissues (FIG. 1C).

Example 3

Figure 2A:
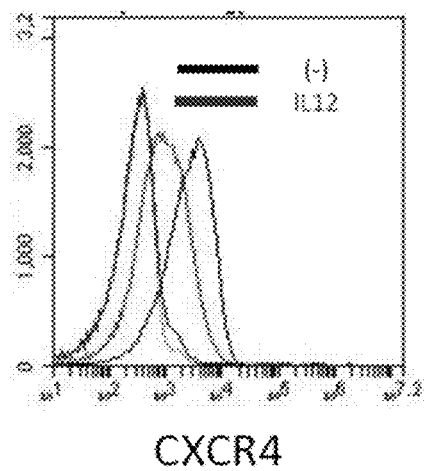
FIG. 2 (A, B) shows that IL-12 suppresses CXCR4 expression in human $CD8^+$ T cells cultured in normoxic conditions. $CD8^+$ T cells were stimulated with anti-CD3/CD28-coated beads in the absence or presence of IL-12 and CXCR4 expression on $CD8^+$ T cells was analyzed by FACS. (A) Representative data from a single experiment with isotype controls. (B) Combined data (mean+/−S.E.) from 5 donors. * p<0.05, by paired Student's t test.
Figure 2B:
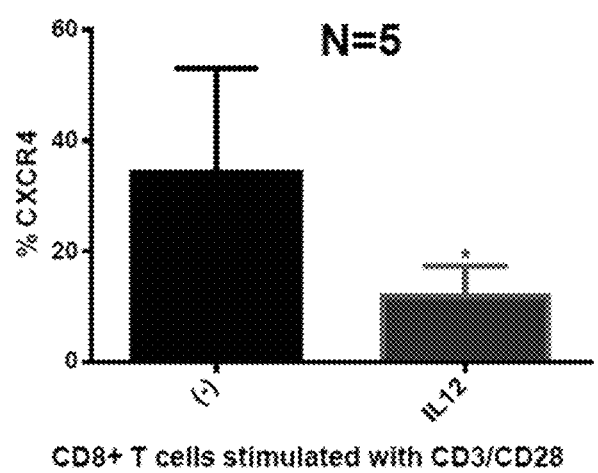
Figure 3A:
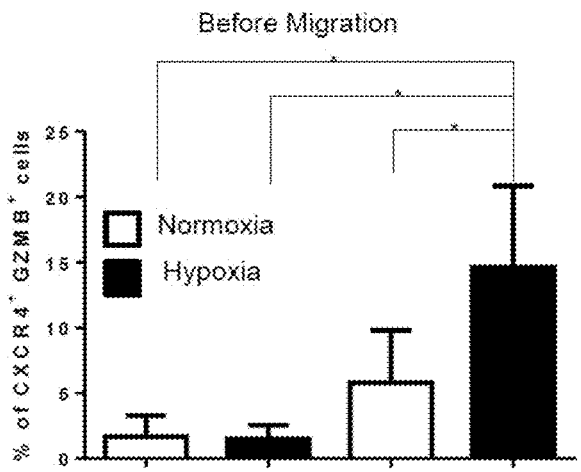
FIG. 3 (A-D) shows that a combination of IL-12 and hypoxia can induce high numbers of $CXCR4^+/GZMB^+$ $CD8^+$ T cells. Naïve $CD8^+$ T cells were stimulated with CD3-CD28 beads, in the presence or absence of IL-12 (5 ng/ml) for 6 days and another 3 days either in normoxia (20%) or hypoxia (1%). The cells were then harvested for FACS staining or analyzed for chemotaxis to 50 ng/ml of CXCL12. Left panel (A) represents % of $CXCR4^+/GZMB^+$ $CD8^+$ T cells induced under various conditions, whereas right panel (B) represents % of $GZMB^+$ $CD8^+$ T cells migrated in response to recombinant CXCL12 (50 ng/ml). Bottom panels (C, D) represent the absolute numbers of $CXCR4^+/GZMB^+$ $CD8^+$ T cells or absolute numbers of migrated $GZMB^+$ $CD8^+$ T cells. *(P<0.05), (P<0.01), *(P<0.001)
Figure 3B:
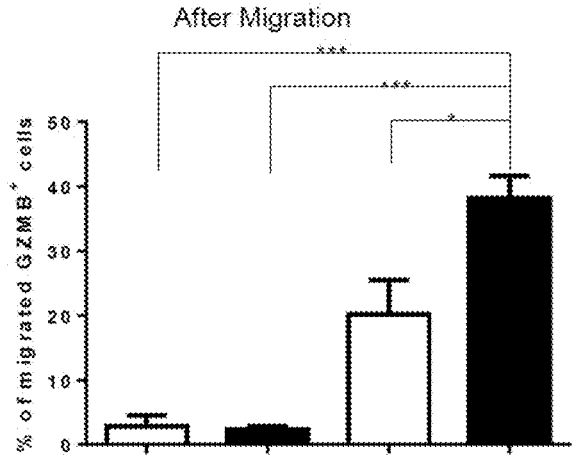
Figure 3C:
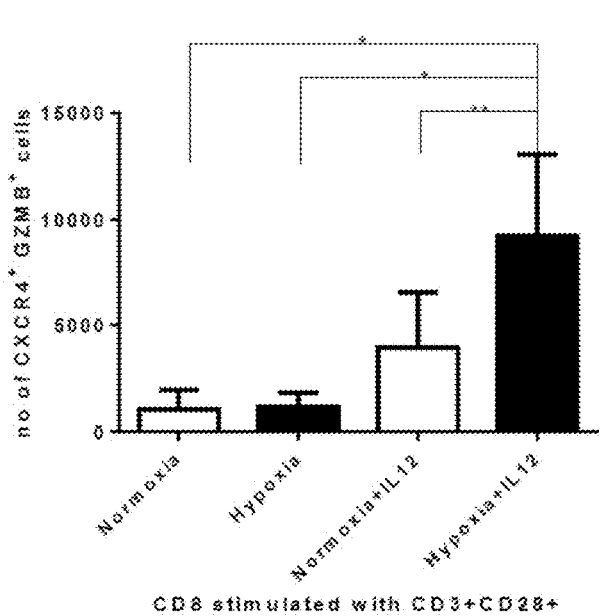
Figure 3D:
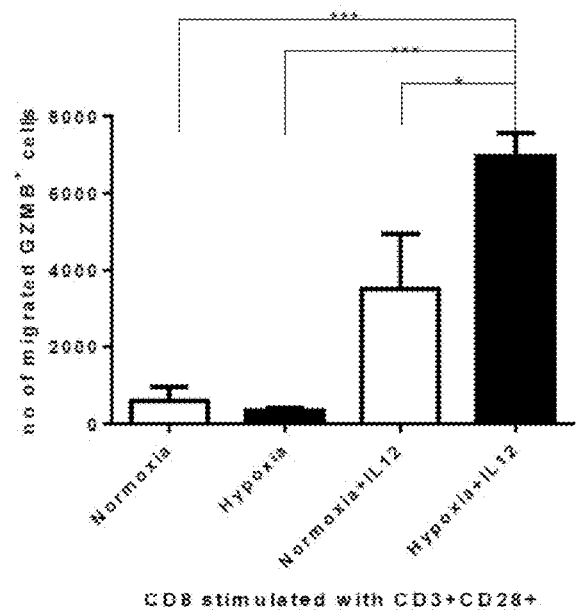
Figure 4A:
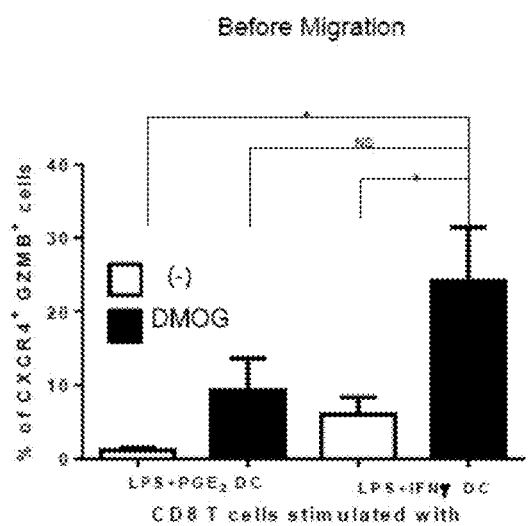
FIG. 4 (A-D) shows that DMOG treatment increases CXCR4 expression and responsiveness to CXCL12 in CTLs activated by CD3/CD28 beads combined with IL-12 or by type-1 polarized DCs. Naïve $CD8^+$ T cells were stimulated with CD3-CD28 beads, in the presence or absence of IL-12 (5 ng/ml) for 6 days and another 3 days in supplementation with or without 200 μM DMOG, then harvested for FACS staining or analyzed for chemotaxis to 50 ng/ml of CXCL12. Left panel (A) represents % of $CXCR4^+/GZMB^+$ double positive $CD8^+$ T cells induced under various conditions, whereas right panel (B) represents % GZMB in $CD8^+$ T cells migrated in response to recombinant CXCL12 (50 ng/ml). Intracellular content of Granzyme B was determined by flow cytometry. Bottom panels (C, D) represent the numbers of $CXCR4^+/GZMB^+$ double positive cells and the numbers of CXCL12 responsive $GZMB^+$ (effector-type) $CD8^+$ T cells. Similar data (not shown) obtained in $CD8^+$ T cells stimulated with SEB-pulsed LPS+IFNγ-matured DC (type-1- polarized DCs) in comparison to LPS+PGE$_2$-matured DC. *(P<0.05), (P<0.01), *(P<0.001), NS (not significant).
Figure 4B:
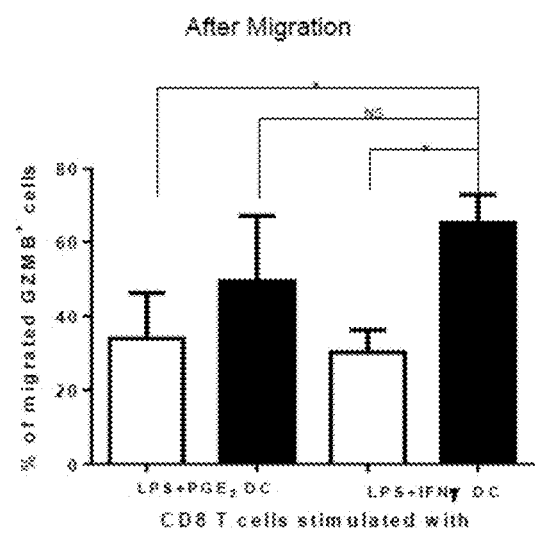
Figure 4C:
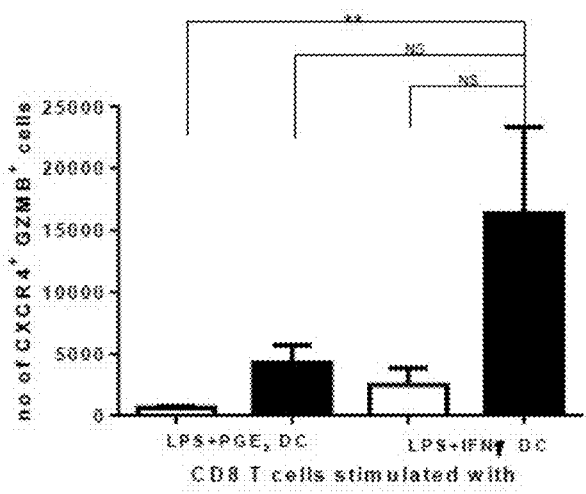
Figure 4D:
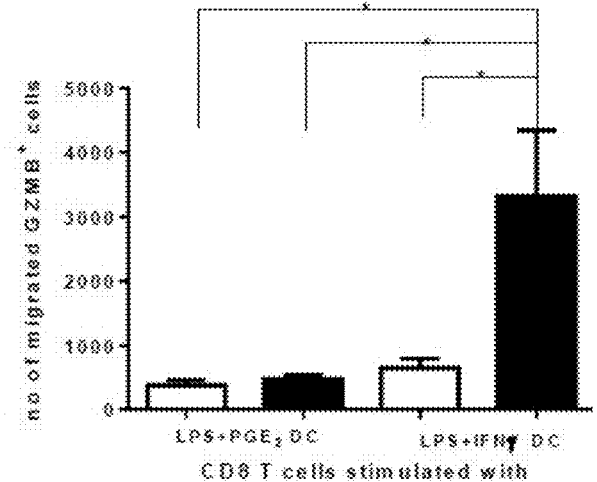

Hypoxia and Small-Molecule HIF-1α Stabilizers Induce Double-Positive CXCR4$^+$/GZMB$^+$ CTL Cells in CTL/Th1-Driving Conditions In accordance with the current paradigm of the regulation of chemokine receptors on pro-inflammatory and non/anti-inflammatory subsets of T cells [Sallusto, F., et al. 1998. Flexible programs of chemokine receptor expression on human polarized T helper 1 and 2 lymphocytes. J. Exp. Med. 187:875-883; Sallusto, F., and Mackay, C. R. 2004. Chemoattractants and their receptors in homeostasis and inflammation. Curr. Opin. Immunol. 16:724-731; Sallusto, F., Mackay, C. R., and Lanzavecchia, A. 1997. Selective expression of the eotaxin receptor CCR3 by human T helper 2 cells. Science 277:2005-2007; Sallusto, F., Mackay, C. R., and Lanzavecchia, A. 2000. The role of chemokine receptors in primary, effector, and memory immune responses. Annu. Rev. Immunol. 18:593-620; Galli, G., et al. 1998. Enhanced HIV expression during Th2-oriented responses explained by the opposite regulatory effect of IL-4 and IFN-gamma of fusin/CXCR4. European journal of immunology 28:3280-3290; Wang, J., et al. 1998. IL-4 and a glucocorticoid up-regulate CXCR4 expression on human CD4$^+$ T lymphocytes and enhance HIV-1 replication. Journal of leukocyte biology 64:642-649], it was observed that the expression of CXCR4 is lost when CD8$^+$ T acquire effector phenotype in response to IL-12 (FIG. 2). Since hypoxia, a formally immunosuppressive condition, has been implicated in several forms of autoimmunity [Beyer, C., Schett, G., Gay, S., Distler, O., and Distler, J. H. 2009. Hypoxia. Hypoxia in the pathogenesis of systemic sclerosis. Arthritis Res. Ther. 11:220; Sica, A., Melillo, G., and Varesio, L. 2011. Hypoxia: a double-edged sword of immunity. J. Mol. Med. (Berl) 89:657-665] and commercially-available hypoxia-mimicking HIF-1α stabilizers (Cobalt chloride-CoC12 and Dimethyloxalylglycine-DMOG) were shown to induce CXCR4 in macrophages, it was determined whether these conditions/factors can be used to induce CXCR4 in Teff cells generated in the presence of IL12 or type-1-polarized DCs and what is their impact on the effector functions of the arising T cells.

The results show that 1% hypoxia or DMOG promote high levels of CXCR4 in CD8$^+$ T cells primed in type-1-polarizing conditions, without affecting the intracellular GZMB expression in arising effector cells (FIGS. 3-4). Migration analysis of the T cells activated under various conditions, demonstrated that T cells induced in type-1-polarizing conditions, by CD3/CD28 plus IL-12 (FIG. 3, 4A) or by high IL-12-producing DCs (FIG. 4B), in the presence of DMOG (FIG. 4), or hypoxia (FIG. 3) showed the highest migration of GZMB$^+$ CTL in response to CXCL12 (FIGS. 3 and 4; right panels).

These results demonstrate the feasibility of using hypoxia or hypoxia mimics to induce CXCR4$^+$/GZMB$^+$ double positive effector CD8$^+$ T cells, without the need for genetic manipulation, and potential for targeting this pathway to manipulate the pathogenic or therapeutic cells in cancer, autoimmunity, allergy and chronic infections.

Example 4

CXCR4$^+$GZMB$^+$ CTLs Induced in Hypoxia-Mimicking Conditions Show Undisturbed High Killer Function To verify that DMOG-induced GZMB$^+$/CXCR4$^+$ CTLs show undisturbed tumor-killing function, the ability of these cells to induce apoptosis (induction of active Caspase-3) was investigated in SEB-loaded target cells (JY-1 cells). As shown in FIG. 5, the cytotoxic function of T cells activated by type-1-polarized (LPS+IFNγ-matured) DCs or T cells activated by LPS+PGE$_2$-matured DC (control, non-polarized DCs) was not affected by DMOG treatment.

Example 5

CXCR4$^+$CD4$^+$T-Bet$^+$ Th1 Cells Induced in Hypoxia-Mimicking Conditions Show Undisturbed High Killer Function To verify that the DMOG/hypoxia-induced CXCR4$^+$ CD4$^+$Th1 cells described above show undisturbed Th1 phenotype, the levels of T-bet were analyzed. As shown in FIG. 6, the levels of T-bet are not suppressed despite the induction of CXCR4 surface expression on CD4$^+$ T cells expanded in hypoxic conditions.

The invention claimed is:

1. A method of making a type-1 polarized active CXCR4+ CD8+ T cell or cell population, a type-1 polarized active CXCR4+ Th1-type-CD4+ T cell or cell population, or a type-1 polarized active CXCR4+ NK cell or cell population, each having increased CXCR4 surface expression as compared to a control, comprising,
   a) providing one or more inactive CD8+ T cells, Th1-type-CD4+ T cells or NK cells, or
   b) providing one or more type-1 polarized active CD8+ T cells, Th1-type-CD4+ T cells or NK cells, and
   c) exposing the cells from step a) to a hypoxic condition and a type-1 polarizing condition, in any order, or
   d) exposing the cells from step b) to a hypoxic condition, and
   e) harvesting the type-1 polarized active CXCR4+CD8+ T cells, type-1 polarized active CXCR4+Th1-type-CD4+ T cells, or type-1 polarized active CXCR4+ NK cells made by performing steps a) and c) or steps b) and d).

2. The method of claim 1, wherein the one or more type-1 polarized active CD8+ T cells, one or more type-1 polarized active Th1-type-CD4+ T cells or one or more type-1 polarized active NK cells from step b) are created by exposing the cells to T cell receptor stimulation, CD3 stimulation and/or CD28 stimulation and one or more type-1 polarizing conditions selected from the group consisting of interleukin 12 receptor stimulation, IFN-γ receptor stimulation, IFN-α/β receptor (type I IFN receptor) stimulation, interleukin 27 receptor stimulation, interleukin 18 receptor stimulation, interleukin 15 receptor stimulation, and CD40 stimulation.

3. The method of claim 1, wherein the hypoxic condition is selected from the group consisting of hypoxia and one or more hypoxia-mimicking compounds.

4. The method of claim 3, wherein the hypoxia is a partial pressure of oxygen less than about 21%.

5. The method of claim 3, wherein the hypoxia is a partial pressure of oxygen less than or about 10%.

6. The method of claim 3, wherein the hypoxia is a partial pressure of oxygen less than or about 5%.

7. The method of claim 3, wherein the hypoxia is a partial pressure of oxygen less than or about 1%.

8. The method of claim 3, wherein the one or more hypoxia-mimicking compounds are HIF1α activators.

9. The method of claim 8, wherein the HIF1α activator is cobalt chloride or dimethyloxalylglycine.

10. The method of claim 1, wherein the harvested active CXCR4$^+$CD8$^+$ T cell or cell population and the active CXCR4$^+$NK cell or cell population is cytotoxic.

11. The method of claim 2, wherein the one or more type-1 polarized active CD8$^+$ T cells, one or more type-1 polarized active Th1-type-CD4$^+$ T cells or one or more type-1polarized active NK cells from step b) are created by exposing the cells to T cell receptor stimulation, CD3 stimulation and/or CD28 stimulation, and interleukin 12 receptor stimulation.

12. The method of claim 1, wherein the type-1 polarizing condition in step c) is exposure of the cells to T cell receptor stimulation, CD3 stimulation and/or CD28stimulation and one or more type-1 polarizing conditions selected from the group consisting of interleukin 12 receptor stimulation, IFN-γ receptor stimulation, IFN-α/βreceptor (type I IFN receptor) stimulation, interleukin 27 receptor stimulation, interleukin 18 receptor stimulation, interleukin 15 receptor stimulation, and CD40stimulation.

13. The method of claim 12, wherein the type-1 polarizing condition in step c) is exposure of the cells to T cell receptor stimulation, CD3 stimulation and/or CD28stimulation, and interleukin 12 receptor stimulation.

\* \* \* \* \*

UNITED STATES PATENT AND TRADEMARK OFFICE
CERTIFICATE OF CORRECTION

PATENT NO. : 10,815,457 B2  Page 1 of 1
APPLICATION NO. : 15/529124
DATED : October 27, 2020
INVENTOR(S) : Pawel Kalinski et al.

It is certified that error appears in the above-identified patent and that said Letters Patent is hereby corrected as shown below:

In the Claims

Column 27, Line 15 should read "stimulation, CD3 stimulation and/or CD28 stimulation and"
Column 27, Line 18 should read "IFN-γ receptor stimulation, IFN-α/β receptor (type I IFN"
Column 27, Line 21 should read "stimulation, and CD40 stimulation."
Column 27, Line 24 should read "stimulation, CD3 stimulation and/or CD28 stimulation, and"

Signed and Sealed this
Twelfth Day of January, 2021

Andrei Iancu
*Director of the United States Patent and Trademark Office*